(12) United States Patent
Watanabe et al.

(10) Patent No.: US 7,012,039 B2
(45) Date of Patent: Mar. 14, 2006

(54) OXIDE CATALYST COMPOSITION

(75) Inventors: Toru Watanabe, Yokohama (JP); Osamu Nagano, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 5 days.

(21) Appl. No.: 10/494,935

(22) PCT Filed: Dec. 20, 2002

(86) PCT No.: PCT/JP02/13369

§ 371 (c)(1), (2), (4) Date: May 7, 2004

(87) PCT Pub. No.: WO03/053570

PCT Pub. Date: Jul. 3, 2003

(65) Prior Publication Data
US 2005/0032639 A1   Feb. 10, 2005

(30) Foreign Application Priority Data
Dec. 21, 2001 (JP) ............................. 2001-388656

(51) Int. Cl.
- B01J 23/00 (2006.01)
- C07C 27/00 (2006.01)
- C07C 69/52 (2006.01)
- C07C 67/00 (2006.01)
- C07C 51/16 (2006.01)

(52) U.S. Cl. .................... 502/300; 502/302; 502/305; 502/311; 502/313; 568/907; 560/205; 560/208; 560/210; 562/545; 562/546; 562/547

(58) Field of Classification Search ................ 502/300, 502/305, 311, 313, 302; 560/205, 208, 210; 562/545–547; 568/907
See application file for complete search history.

(56) References Cited

U.S. PATENT DOCUMENTS

| | | | |
|---|---|---|---|
| 3,928,462 A | 12/1975 | Shiraishi et al. | |
| 4,001,317 A | 1/1977 | Grasselli et al. | |
| 4,249,019 A | 2/1981 | Tamura et al. | |
| 4,479,013 A * | 10/1984 | Khoobiar | 568/479 |
| 4,518,796 A | 5/1985 | Aoshima et al. | |

(Continued)

FOREIGN PATENT DOCUMENTS

EP   1055455 A2   11/2000

(Continued)

OTHER PUBLICATIONS

"Sekiyu Kagaku Purosesu (Petrochemical Process)", published by Kodansha Scientific, Inc., Japan, pp. 172 to 176 (Aug. 10, 2001).

*Primary Examiner*—J. A. Lorengo
*Assistant Examiner*—Patricia L. Hailey
(74) *Attorney, Agent, or Firm*—Birch, Stewart, Kolasch & Birch, LLP

(57) ABSTRACT

An oxide catalyst composition for use in producing methacrolein or a mixture of methacrolein and methacrylic acid, wherein the oxide catalyst composition is represented by the formula $(Mo+W)_{12}Bi_aA_bB_cFe_dX_eSb_fO_g$, wherein: A is at least one member selected from the group consisting of Y and the elements of the lanthanoid series exclusive of Pm; B is at least one member selected from the group consisting of K, Rb and Cs; X is Co solely, or a mixture of Co and at least one member selected from the group consisting of Mg and Ni; and a, b, c, d, e, f and g are, respectively, the atomic ratios of Bi, A, B, Fe, X, Sb and O, relative to twelve atoms of the total of Mo and W, wherein the atomic ratios (a to f) of the elements and the relationship between the amounts of the elements are chosen so as to satisfy specific requirements.

8 Claims, 1 Drawing Sheet

U.S. PATENT DOCUMENTS

| | | |
|---|---|---|
| 4,537,874 A | 8/1985 | Sato et al. |
| 4,743,706 A * | 5/1988 | Guttmann et al. .......... 560/214 |
| 5,250,485 A * | 10/1993 | Kuroda et al. .............. 502/159 |
| 5,264,627 A | 11/1993 | Tazaki et al. |
| 5,728,894 A * | 3/1998 | Nagano et al. ............. 568/479 |
| 5,969,178 A * | 10/1999 | Okamoto et al. .......... 560/208 |
| 6,383,973 B1 | 5/2002 | Kimura et al. |
| 6,740,769 B1 * | 5/2004 | Mizutani et al. ............ 558/324 |
| 2002/0188151 A1 * | 12/2002 | Inoue et al. ................ 560/205 |

FOREIGN PATENT DOCUMENTS

| | | |
|---|---|---|
| JP | 48-17253 | 5/1973 |
| JP | 51-12605 | 4/1976 |
| JP | 51-13125 | 4/1976 |
| JP | 53-23809 | 7/1978 |
| JP | 57-35859 B2 | 7/1982 |
| JP | 57-61011 B2 | 12/1982 |
| JP | 60-163830 A | 8/1985 |
| JP | 63-122641 A | 5/1988 |
| JP | 2-227140 A | 9/1990 |
| JP | 5-86939 B2 | 12/1993 |
| JP | 8-309192 A | 11/1996 |
| JP | 10-216523 A | 8/1998 |
| WO | WO 95/35273 A1 | 12/1995 |

* cited by examiner

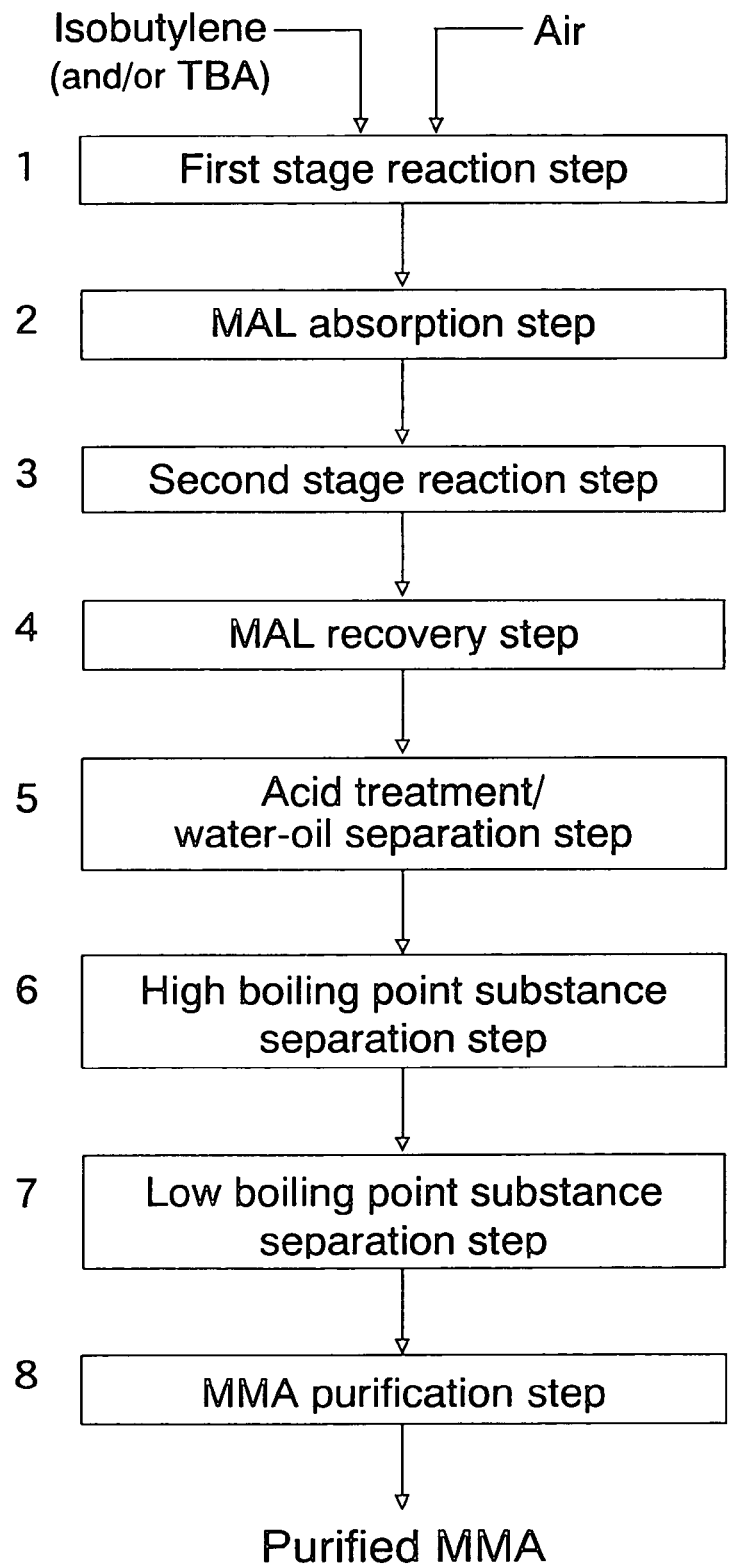
Figure

OXIDE CATALYST COMPOSITION

BACKGROUND OF THE INVENTION

1. Field of the Invention

The present invention relates to an oxide catalyst composition. More particularly, the present invention is concerned with an oxide catalyst composition for use in producing methacrolein or a mixture of methacrolein and methacrylic acid by reacting at least one member selected from the group consisting of isobutylene and t-butanol with a molecular oxygen-containing gas, wherein the oxide catalyst composition comprises, in specific ratios, molybdenum or a mixture of molybdenum and tungsten; bismuth; iron; antimony; at least one member selected from the group consisting of yttrium and the elements of the lanthanoid series exclusive of promethium; and at least one member selected from the group consisting of potassium, rubidium and cesium; and cobalt solely, or a mixture of cobalt and at least one member selected from the group consisting of magnesium and nickel.

The oxide catalyst composition of the present invention exhibits not only a prolonged catalyst life due to its excellent properties with respect to thermal stability and reduction resistance, but also excellent selectivity for the desired product. By the use of the oxide catalyst composition of the present invention for producing methacrolein or a mixture of methacrolein and methacrylic acid, it becomes possible to stably produce the desired product for a long time while holding down the amount of by-produced impurities, e.g. diacetyl. The produced methacrolein or mixture of methacrolein and methacrylic acid has low contents of the by-produced impurities, e.g. diacetyl, and such methacrolein or mixture of methacrolein and methacrylic acid is very advantageous as a raw material for producing methyl methacrylate having excellent transparency. A methyl methacrylate polymer having excellent transparency, which can be obtained by polymerizing such highly transparent methyl methacrylate monomer, can be advantageously used as a substitute for glass and quartz in application fields requiring high transparency, such as optical fibers, light guide plates and the like; thus, such highly transparent methyl methacrylate polymer has very high commercial value.

2. Prior Art

A polymer produced from methyl methacrylate is characterized in that it is glassy, hard and transparent, and such polymer is frequently used as a substitute for glass. In recent years, in the fields related to optical fibers, a methyl methacrylate polymer is attracting attention as an optical material which can substitute for quartz, and the use of the methyl methacrylate polymer is spreading. Therefore, the methyl methacrylate polymer used as a substitute for glass or quartz is required to have high transparency and high weathering resistance. For obtaining such an excellent methyl methacrylate polymer, it is important that, in a methyl methacrylate monomer used as the raw material therefor, the amounts of trace impurities be very small which lower the transparency and weathering resistance of the methyl methacrylate polymer.

As methods for producing methyl methacrylate, which is a compound highly useful in the industry, there are known two methods: a "direct ML-to-MMA process" comprising two reaction steps and a "via methacrylic acid process" comprising three reaction steps. The direct ML-to-MMA process comprises two catalytic reaction steps, wherein the first reaction step comprises subjecting isobutylene and/or t-butanol as a starting material to a gaseous phase catalytic oxidation reaction with a molecular oxygen-containing gas in the presence of an oxide catalyst (hereinafter, this catalyst is frequently referred to as a "first stage catalyst") to thereby obtain methacrolein, and the second reaction step comprises subjecting the obtained methacrolein to a gaseous phase catalytic reaction with methanol and a molecular oxygen-containing gas in the presence of a carrier-supported catalyst containing palladium (hereinafter, this catalyst is frequently referred to as a "second stage catalyst"), to thereby produce methyl methacrylate (MMA) by one step directly from methacrolein (ML).

In the recent studies by the present inventors on the direct ML-to-MMA process, it has been found that substances which show an absorption in the visible light range of 400 nm to 780 nm, are causative of discoloration of methyl methacrylate. The substances showing an absorption in the visible light range include not only diacetyl, which is conventionally known as being causative of discoloration, but also pyruvic aldehyde, 2-acetylfuran and the like. Thus, pyruvic aldehyde, 2-acetylfuran and the like have been found to be substances causative of the discoloration of methyl methacrylate.

The first stage catalyst used in the direct ML-to-MMA process (wherein the first stage catalyst is used for producing methacrolein by subjecting at least one member selected from the group consisting of isobutylene and t-butanol to a gaseous phase catalytic oxidation reaction with a molecular oxygen-containing gas) was proposed by the present inventors (see, for example, International Patent Application Publication No. WO 95/35273 and Unexamined Japanese Patent Application Laid-Open Specification No. Hei 10-216523). However, at the time of the development of the catalyst, it was not well recognized that the impurities, e.g. diacetyl, which are by-produced by the catalyst are causative of the discoloration of methyl methacrylate.

U.S. Pat. No. 4,249,019, Japanese Patent Application Publication No. Sho 57-35859, U.S. Pat. No. 4,518,796 and the like propose various types of palladium-containing second stage catalyst for use in the second reaction step of the direct ML-to-MMA process (wherein the second stage catalyst is used for producing methyl methacrylate by subjecting methacrolein to a gaseous phase catalytic reaction with methanol and a molecular oxygen-containing gas). In the studies of the present inventors, it has been found that, since the second stage catalytic reaction (for producing methyl methacrylate by reacting methacrolein, methanol and a molecular oxygen-containing gas) is conducted under moderate reaction conditions wherein the reaction temperature is in the range of from room temperature to 100° C., the impurities, e.g. diacetyl, which would be causative of the discoloration of the resultant methyl methacrylate remain almost unreacted and undecomposed during the second stage catalytic reaction, and the impurities as such are carried over into a subsequent purification step. When the impurities causative of discoloration are carried over into the purification step, it is necessary to perform repeatedly the purification operation for removing the impurities from the methyl methacrylate. As a result, great commercial disadvantages are posed in that the repeated purification operation causes a loss of methyl methacrylate, leading to an increase in the production cost.

The via methacrylic acid process is also a method for producing methyl methacrylate by using isobutylene and/or t-butanol as a starting material. The via methacrylic acid process is described at pages 172 to 176 of "Sekiyu Kagaku Purosesu (Petrochemical Process)", published by Kodansha Scientific, Inc., Japan. The document states that the via methacrylic acid process comprises three reaction steps, that is, a first oxidation step, a second oxidation step, and an esterification step. The first oxidation step is a step of subjecting at least one starting material selected from the group consisting of isobutylene and t-butanol to a gaseous phase catalytic oxidation reaction with molecular oxygen in the presence of a catalyst, to thereby obtain methacrolein. The second oxidation step is a step of subjecting the methacrolein obtained in the first oxidation step to a gaseous phase catalytic oxidation reaction with molecular oxygen in the presence of a catalyst, to thereby obtain methacrylic acid. The esterification step is a step of subjecting the methacrylic acid obtained in the second oxidation step to esterification, to thereby obtain methyl methacrylate.

Various proposals have been made on the catalyst used in the first oxidation step of the via methacrylic acid process, that is, the catalyst used for producing methacrolein by subjecting at least one starting material selected from the group consisting of isobutylene and t-butanol to a gaseous phase catalytic oxidation reaction. Most of such proposals are concerned with the selection of the types and ratios of the components of the catalyst. For example, there can be mentioned Examined Japanese Patent Application Publication No. Sho 48-17253 (corresponding to Canadian Patent No. 947,772), U.S. Pat. Nos. 4,001,317 and 4,537,874, and Unexamined Japanese Patent Application Laid-Open Specification Nos. Sho 60-163830, Sho 63-122641 and Hei 2-227140. The catalysts disclosed in these patent documents are aimed mainly at achieving an improved yield of the desired product; and, in these patent documents, the experimental data concerning the performance of the catalysts are only the data of the conversion of isobutylene and t-butanol and the data of the yield of and selectivity for methacrolein or methacrylic acid.

With respect to the by-produced impurities formed in the via methacrylic acid process (that is, the products other than methacrolein and methacrylic acid which are, respectively, the desired products of the first and second oxidation steps of the via methacrylic acid process), the descriptions of prior art documents are as follows. For example, Examined Japanese Patent Application Publication No. Sho 53-23809 describes the selectivities for acetic acid, $CO_2$ and CO; Examined Japanese Patent Application Publication No. Sho 57-61011 describes the selectivities for acetone and acetic acid; and Examined Japanese Patent Application Publication Nos. Sho 51-13125 and Sho 51-12605 each describe the selectivities for $CO_2$ and CO. In addition, U.S. Pat. No. 3,928,462 (corresponding to Examined Japanese Patent Application Publication Nos. Sho 47-32043 and Sho 47-32044) describes that the selectivity for acrolein is 5% to 6%. All of the impurities described in the above-mentioned patent documents are different from the substances which are causative of discoloration.

In addition, Examined Japanese Patent Application Publication No. Hei 5-86939 describes that a gaseous, oxidation reaction product, which is obtained by subjecting at least one member selected from the group consisting of isobutylene and t-butanol to a gaseous phase catalytic oxidation for producing methacrolein, contains not only methacrolein and methacrylic acid, but also low boiling point by-products (such as acetoaldehyde, acetone, acrolein, acetic acid and acrylic acid), high boiling point by-products (such as maleic acid and aromatic carboxylic acids), polymeric substances and tarry substances. For obtaining a gaseous, oxidation reaction product containing substantially no polymeric substances and the like, the above-mentioned patent document proposes a method in which the gaseous, oxidation reaction product is contacted with a solid alkaline earth metal compound to thereby suppress the formation of the polymeric substances and the like, and also proposes a method in which the polymeric substances and the like contained in the gaseous, oxidation reaction product are decomposed and removed therefrom. This patent document describes the amounts of the by-produced maleic acid and the by-produced polymeric substances, in addition to the amounts of the produced methacrolein and the produced methacrylic acid. However, this patent document has no description about the trace impurities which are causative of the discoloration of methyl methacrylate.

In addition, it is considered that, since a high reaction temperature, namely 300° C. to 400° C., is used in the second oxidation step of the via methacrylic acid process, most of the substances (such as diacetyl) causative of discoloration which are by-produced in the first oxidation step are decomposed during the second oxidation step of the via methacrylic acid process. Consequently, the substances causative of discoloration have not been particularly considered as being a problem in the case of the via methacrylic acid process. However, since not all of the substances causative of discoloration are decomposed in the second oxidation step of the via methacrylic acid process, it is necessary that a catalyst which does not by-produce the substances causative of discoloration be used in the first oxidation step of the via methacrylic acid process.

In connection with the first and second oxidation steps of the via methacrylic acid process, Japanese Patent No. 2509049 (corresponding to U.S. Pat. No. 5,264,627) describes a measure for reducing the amounts of the impurities which are causative of the discoloration of methyl methacrylate. In this patent document, the via methacrylic acid process is performed as follows. At least one compound selected from the group consisting of isobutylene, t-butanol and methyl-t-butyl ether is introduced, together with molecular oxygen, into a shell-and-tube heat exchanger type first oxidation reactor packed with an oxide catalyst containing bismuth, molybdenum and iron, and a gaseous phase catalytic oxidation reaction is effected therein to thereby obtain a gaseous reaction product comprised mainly of methacrolein. Subsequently, the methacrolein-containing gaseous reaction product and molecular oxygen are introduced into a shell-and-tube heat exchanger type second reactor packed with an oxide catalyst containing molybdenum and phosphorus, and a gaseous phase catalytic oxidation reaction is effected therein to thereby produce a gaseous reaction product comprised mainly of methacrylic acid. In this method, the space of the gas outlet portion of the second reactor is packed with a solid packing so as to reduce the volume of the space (of the gas outlet portion) which is present downstream of the catalyst bed in the second reactor, wherein the reduction of the volume of the space of the gas outlet portion is intended to shorten the residence time of the gaseous reaction product in the space of the gas outlet portion, thereby suppressing the by-production of diketones. This patent document further states that, when diketones are contained in methacrylic acid obtained after the first and second oxidation steps, a problem arises in that the diketones are converted into furan compounds in the final methacrylate polymer and the furan compounds cause discoloration of the polymer. (In the Working Examples of this patent document, acetonitrile acetone is mentioned as a diketone.)

Therefore, when the catalyst used in the first reactor used in the above-described method is improved so as to decrease the amount of the by-produced diketones, the improved catalyst is effective for decreasing the amounts of the substances causative of the discoloration of methyl methacrylate produced by the via methacrylic acid process.

As can be seen from the descriptions of the above-mentioned patent documents, it has been recognized to some extent that the discoloration of methyl methacrylate produced by the via methacrylic acid process is caused by the impurities, e.g. diacetyl, which are by-produced in the first oxidation step of the via methacrylic acid process, namely by-produced in a reaction in which at least one member selected from the group consisting of isobutylene and t-butanol is subjected to a gaseous phase catalytic oxidation reaction in the presence of a catalyst, thereby producing methacrolein. However, there have been no methods for improving the catalyst used for producing methacrolein in the first oxidation step of the via methacrylic acid process wherein the improvement is for decreasing the amounts of the substances (such as diacetyl) causative of discoloration which are by-produced in the first oxidation step of the via methacrylic acid process.

When methyl methacrylate is produced by the direct ML-to-MMA process, oxidative methyl esterification (the second stage reaction) is conducted at a low temperature (room temperature to 100° C.). The advantage of the direct ML-to-MMA process is that the yield of methyl methacrylate is higher than in the case of the via methacrylic acid process. However, the direct ML-to-MMA process has a problem in that most of the substances (such as diacetyl) causative of discoloration are not decomposed by the second stage reaction catalyst and are carried over into the subsequent purification step. Therefore, in the direct ML-to-MMA process, for improving the quality of methyl methacrylate, it is necessary to decrease the amount of the substances causative of discoloration, which are impurities by-produced in the first stage reaction. Thus, there is a strong demand for the development of a catalyst which is advantageous not only in that a high selectivity for methacrolein can be achieved, but also in that the catalyst has high thermal stability and high reduction resistance, and the selectivity for the impurities causative of discoloration can be held down to a minimum level.

SUMMARY OF THE INVENTION

In this situation, the present inventors have made extensive and intensive studies toward developing an oxide catalyst which is advantageous not only in that a high selectivity for methacrolein can be achieved, but also in that the catalyst has high thermal stability and high reduction resistance, and the selectivity for the impurities causative of discoloration can be held down to a minimum level. As a result, it has unexpectedly been found that the above-mentioned object can be attained by an oxide catalyst composition which comprises molybdenum or a mixture of molybdenum and tungsten; bismuth; iron; antimony; at least one member selected from the group consisting of yttrium and the elements of the lanthanoid series exclusive of promethium; and at least one member selected from the group consisting of potassium, rubidium and cesium; and cobalt solely, or a mixture of cobalt and at least one member selected from the group consisting of magnesium and nickel, wherein the respective atomic ratios of the above-mentioned elements and the relationship between the amounts of the above-mentioned elements are chosen so as to satisfy specific requirements. That is, it has unexpectedly been found that such oxide catalyst composition exhibits not only a prolonged catalyst life due to its excellent properties with respect to thermal stability and reduction resistance, but also a high selectivity for methacrolein and a low selectivity for the impurities which are causative of discoloration of methyl methacrylate. The present invention has been completed, based on this novel finding.

Accordingly, it is a primary object of the present invention to provide an oxide catalyst composition for use in producing methacrolein or a mixture of methacrolein and methacrylic acid wherein the methacrolein or mixture has low impurity content and is very advantageous as a raw material for producing a highly transparent methyl methacrylate.

The foregoing and other objects, features and advantages of the present invention will be apparent to those skilled in the art from the following detailed description taken in connection with the accompanying drawing and the appended claims.

BRIEF DESCRIPTION OF THE DRAWING

FIGURE is a flow chart showing the steps of the direct ML-to-MMA process conducted in the Examples for producing methyl methacrylate.

DESCRIPTION OF REFERENCE NUMERALS

1: First stage reaction step
2: Methacrolein (MAL) absorption step
3: Second stage reaction step
4: Methacrolein (MAL) recovery step
5: Acid treatment/water-oil separation step
6: High boiling point substance separation step
7: Low boiling point substance separation step
8: Methyl methacrylate (MMA) purification step

DETAILED DESCRIPTION OF THE INVENTION

According to the present invention, there is provided an oxide catalyst composition for use in producing methacrolein or a mixture of methacrolein and methacrylic acid by reacting at least one member selected from the group consisting of isobutylene and t-butanol with a molecular oxygen-containing gas, the oxide catalyst composition being represented by the following formula (I):

$$(Mo+W)_{12}Bi_aA_bB_cFe_dX_eSb_fO_g \qquad (I)$$

wherein:
A is at least one member selected from the group consisting of lanthanum, cerium, praseodymium, neodymium, samarium, europium, gadolinium, terbium, dysprosium, holmium, erbium, thulium, ytterbium, lutetium and yttrium;
B is at least one member selected from the group consisting of potassium, rubidium and cesium;
X is cobalt solely, or a mixture of cobalt and at least one member selected from the group consisting of magnesium and nickel;
wherein the number of molybdenum (Mo) atoms is in the range of from more than 9 to 12, and the number of tungsten (W) atoms is in the range of from 0 to less than 3, each relative to twelve atoms of the total of molybdenum (Mo) and tungsten (W); and
a, b, c, d, e, f and g are, respectively, the atomic ratios of bismuth (Bi), A, B, iron (Fe), X, antimony (Sb) and oxygen (O), relative to twelve atoms of the total of molybdenum (Mo) and tungsten (W),
wherein
$0 < a \leq 8$, $0<b\leq 8$,
$0<c<3$,
$0.2<d<5$,
$1\leq e\leq 12$,
$0.1<f<3$, and
g is the number of oxygen atoms required to satisfy the valence requirements of the other elements present; and wherein a, b, c, d and f satisfy the requirements of the following formulae:

$0.02<b/(a+b+c)<0.6$, $0<c/(a+b+c)\leq 0.9$, $0.01<d/(a+b+d)\leq 0.9$, and $0.1<d-f<2.5$.

For easy understanding of the present invention, the essential features and various preferred embodiments of the present invention are enumerated below.

1. An oxide catalyst composition for use in producing methacrolein or a mixture of methacrolein and methacrylic acid by reacting at least one member selected from the group consisting of isobutylene and t-butanol with a molecular oxygen-containing gas, the oxide catalyst composition being represented by the following formula (I):

   (I)

wherein:
A is at least one member selected from the group consisting of lanthanum, cerium, praseodymium, neodymium, samarium, europium, gadolinium, terbium, dysprosium, holmium, erbium, thulium, ytterbium, lutetium and yttrium;
B is at least one member selected from the group consisting of potassium, rubidium and cesium;
X is cobalt solely, or a mixture of cobalt and at least one member selected from the group consisting of magnesium and nickel;
wherein the number of molybdenum (Mo) atoms is in the range of from more than 9 to 12, and the number of tungsten (W) atoms is in the range of from 0 to less than 3, each relative to twelve atoms of the total of molybdenum (Mo) and tungsten (W); and
a, b, c, d, e, f and g are, respectively, the atomic ratios of bismuth (Bi), A, B, iron (Fe), X, antimony (Sb) and oxygen (O), relative to twelve atoms of the total of molybdenum (Mo) and tungsten (W),
wherein
$0<a\leq 8$,
$0<b\leq 8$,
$0<c<3$,
$0.2<d<5$,
$1\leq e\leq 12$,
$0.1<f<3$, and
g is the number of oxygen atoms required to satisfy the valence requirements of the other elements present; and wherein a, b, c, d and f satisfy the requirements of the following formulae:

$0.02<b/(a+b+c)<0.6$, $0<c/(a+b+c)\leq 0.9$, $0.01<d/(a+b+d)\leq 0.9$, and $0.1<d-f<2.5$.

2. The oxide catalyst composition according to item 1 above, wherein, in the mixture X in formula (I), the atomic ratio of cobalt to the total of cobalt, magnesium and nickel is 0.5 or more,
wherein, when the mixture X in formula (I) contains magnesium, the atomic ratio of magnesium to the total of cobalt, magnesium and nickel in the mixture X is 0.5 or less, and
wherein, when the mixture X in formula (I) contains nickel, the atomic ratio of nickel to the total of cobalt, magnesium and nickel in the mixture X is less than 0.33.

3. The oxide catalyst composition according to item 1 or 2 above, wherein a, b and c in formula (I) satisfy the requirements of the formula: $0.05<b/(a+b+c)<0.5$.

4. The oxide catalyst composition according to any one of items 1 to 3 above, wherein a, b and c in formula (I) satisfy the requirements of the formula: $0.1<c/(a+b+c)<0.8$.

5. The oxide catalyst composition according to any one of items 1 to 4 above, wherein a, b, d and f in formula (I) satisfy the requirements of the formulae:

$0.2<d/(a+b+d)<0.9$ and $0.3\leq d-f\leq 2.3$.

Hereinbelow, the present invention will be described in detail.

The oxide catalyst composition of the present invention is represented by the following formula (I):

   (I)

wherein:
A is at least one member selected from the group consisting of lanthanum, cerium, praseodymium, neodymium, samarium, europium, gadolinium, terbium, dysprosium, holmium, erbium, thulium, ytterbium, lutetium and yttrium;
B is at least one member selected from the group consisting of potassium, rubidium and cesium;
X is cobalt solely, or a mixture of cobalt and at least one member selected from the group consisting of magnesium and nickel;
wherein the number of molybdenum (Mo) atoms is in the range of from more than 9 to 12, and the number of tungsten (W) atoms is in the range of from 0 to less than 3, each relative to twelve atoms of the total of molybdenum (Mo) and tungsten (W); and
a, b, c, d, e, f and g are, respectively, the atomic ratios of bismuth (Bi), A, B, iron (Fe), X, antimony (Sb) and oxygen (O), relative to twelve atoms of the total of molybdenum (Mo) and tungsten (W),
wherein
$0<a\leq 8$,
$0<b\leq 8$,
$0<c<3$,
$0.2<d<5$,
$1\leq e\leq 12$,
$0.1<f<3$, and
g is the number of oxygen atoms required to satisfy the valence requirements of the other elements present, and wherein a, b, c, d and f satisfy the requirements of the following formulae:

$0.02<b/(a+b+c)<0.6$, $0<c/(a+b+c)\leq 0.9$, $0.01<d/(a+b+d)\leq 0.9$, and $0.1<d-f<2.5$.

In the present invention, molybdenum (Mo) is an indispensable component for the oxide catalyst composition, but tungsten (W) may be used in partial substitution for molybdenum. The number of molybdenum atoms is in the range of from more than 9 to 12, preferably from more than 9.5 to 12, and the number of tungsten atoms is in the range of from 0 to less than 3, preferably from 0 to less than 2.5, each relative to twelve atoms of the total of molybdenum and tungsten.

In the present invention, bismuth (Bi) is indispensable for the synthesis of methacrolein. For providing an oxide catalyst composition capable of achieving the catalytic performances aimed at in the present invention, it is necessary that the atomic ratio (a) of bismuth, relative to twelve atoms of the total of molybdenum and tungsten, satisfy the relationship $0 < a \leq 8$.

A in formula (I) is at least one member selected from the group consisting of yttrium and the elements of the lanthanoid series exclusive of promethium, that is, at least one member selected from the group consisting of lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu) and yttrium (Y). Element A is indispensable for imparting excellent thermal stability and reduction resistance to the oxide catalyst composition. For attaining this purpose, it is necessary that the atomic ratio (b) of A, relative to twelve atoms of the total of molybdenum and tungsten, satisfy the relationship $0 < b \leq 8$.

B in formula (I) is at least one member selected from the group consisting of potassium (K), rubidium (Rb) and cesium (Cs). Element B is indispensable for not only further enhancing the effect of addition of element A, but also for improving the selectivity for methacrolein. For attaining these purposes, it is necessary that the atomic ratio (c) of B, relative to twelve atoms of the total of molybdenum and tungsten, satisfy the relationship $0 < c < 3$. When the atomic ratio (c) of B becomes 3 or more, it becomes impossible to obtain an oxide catalyst composition having the desired catalytic activity even if not only the amount of at least one element selected from the group consisting of potassium (K), rubidium (Rb) and cesium (Cs), but also the calcination and firing temperatures are appropriately regulated. For obtaining an oxide catalyst composition having the desired catalytic activity, it is preferred that the atomic ratio (c) of B, relative to twelve atoms of the total of molybdenum and tungsten, is in the range of from more than 0 to less than 2.0, more advantageously from more than 0 to less than 1.5, still more advantageously from more than 0 to less than 1.2.

In the present invention, for obtaining remarkable improvements in the thermal stability and reduction resistance by the addition of element A (i.e., at least one member selected from the group consisting of La, Ce, Pr, Nd, Sm, Eu, Gd, Tb, Dy, Ho, Er, Tm, Yb, Lu and Y), while maintaining the high selectivity for methacrolein, it is important to adjust the relationship between the amounts of element A, bismuth (Bi) and element B (i.e., at least one element selected from the group consisting of potassium, rubidium and cesium). Specifically, it is important that the atomic ratios a, b and c in formula (I) satisfy the relationship $0.02 < b/(a+b+c) < 0.6$, preferably $0.05 < b/(a+b+c) < 0.5$.

In addition, for synergistically improving the effect of adding element B, it is important to adjust the relationship between the amounts of element B, bismuth and element A. Specifically, it is important that the atomic ratios a, b and c in formula (I) satisfy the relationship $0 < c/(a+b+c) \leq 0.9$, preferably $0.1 < c/(a+b+c) < 0.8$.

The reason why the excellent performances aimed at in the present invention can be achieved when amounts of bismuth, element A and element B satisfy the above-mentioned requirements has not yet been elucidated. However, the reason is believed to be as follows. When bismuth, element A and element B are used so as to satisfy a specific relationship, molybdic acid compounds respectively of bismuth, element A and element B (or such molybdic acid compounds as well as tungstenic acid compounds respectively of bismuth, element A and element B when tungsten is also contained in the oxide catalyst composition) undergo solid solubilization, thereby exhibiting advantageous performances desired in the present invention.

In the present invention, iron (Fe) is indispensable, similarly to bismuth, for commercial scale synthesis of methacrolein. However, when too large an amount of iron is contained in the oxide catalyst composition, the amount of by-products, such as CO and $CO_2$, is likely to increase, thus lowering the selectivity for methacrolein. Therefore, it is necessary that the atomic ratio (d) of iron, relative to twelve atoms of the total of molybdenum and tungsten, is in the range of from $0.2 < d < 5$.

Further, with respect to the iron component, it is important to adjust the relationship between the amounts of iron, bismuth and element A, and it is necessary that the atomic ratios a, b and d in formula (I) satisfy the relationship $0.01 < d/(a+b+d) \leq 0.9$, preferably $0.2 < d/(a+b+d) < 0.9$. From the viewpoint of achieving high selectivity for methacrolein, it is preferred that the atomic ratios a, b and d, relative to twelve atoms of the total of molybdenum and tungsten, satisfy the relationships $0.2 < d < 5$ and $0 < d/(a+b+d) \leq 0.9$, more preferably $0.2 < d \leq 4$ and $0.01 < d/(a+b+d) \leq 0.9$, still more preferably $0.2 < d \leq 4$ and $0.2 < d/(a+b+d) < 0.9$.

In the oxide catalyst composition of the present invention which is represented by formula (I), X is cobalt solely, or a mixture of cobalt and at least one member selected from the group consisting of magnesium and nickel. Cobalt (Co) X in formula (I) is indispensable for improving the catalytic activity of the oxide catalyst composition without lowering the selectivity for methacrolein. Specifically, it is necessary that the atomic ratio (e) of X, relative to twelve atoms of the total of molybdenum and tungsten, satisfy the relationship $1 \leq e \leq 12$.

In X of formula (I), magnesium (Mg) and nickel (Ni) are elements which can be used in partial substitution for the cobalt component. With respect to the cost of a starting material, a magnesium material and a nickel material are less expensive than a cobalt material. Therefore, it is commercially advantageous that magnesium and/or nickel can be used in partial substitution for the cobalt component, from the viewpoint of reduction of catalyst production cost. However, if magnesium, nickel or a mixture of magnesium and nickel is used as X without being combined with cobalt, it is impossible to satisfactorily improve the catalytic activity of the oxide catalyst composition. In the mixture X in formula (I), it is preferred that the atomic ratio of cobalt to the total of cobalt, magnesium and nickel is 0.5 or more. When the mixture X in formula (I) contains magnesium, the atomic ratio of magnesium to the total of cobalt, magnesium and nickel in the mixture X is preferably 0.5 or less. When the mixture X in formula (I) contains nickel, the atomic ratio of nickel to the total of cobalt, magnesium and nickel in the mixture X is preferably less than 0.33.

In the present invention, antimony (Sb) is indispensable for suppressing the selectivity for diacetyl and by-produced aldehydes, such as acetoaldehyde and acrolein. Specifically, it is necessary that the atomic ratio (f) of antimony, relative to twelve atoms of the total of molybdenum and tungsten, satisfy the relationship 0.1<f<3. For further improving the catalytic activity of the oxide catalyst composition, it is preferred that the atomic ratio (f) of antimony satisfies the relationship $0.3 \leq f \leq 2.5$.

For maintaining the selectivity for methacrolein, it is necessary that the amounts of antimony and iron satisfy a specific relationship. Specifically, it is necessary that d and f in formula (I) satisfy the relationship 0.1<d−f<2.5. For further improving the catalytic activity of the oxide catalyst composition, it is preferred that d and f in formula (I) satisfy the relationship $0.3 \leq d-f \leq 2.3$.

In addition, from the viewpoint of achieving a high selectivity for methacrolein, it is preferred that the atomic ratio (d) of iron and the atomic ratio (f) of antimony satisfy the relationships $0.3 \leq d-f \leq 2.3$ and $0.2 < d/(a+b+d) < 0.9$ simultaneously.

Next, methods for producing the oxide catalyst composition of the present invention are explained in detail.

With respect to the methods for producing the oxide catalyst composition of the present invention, there is no particular limitation, and any conventional method can be used as long as it enables the production of an oxide represented by formula (I) above. For example, the oxide catalyst composition of the present invention can be produced by a method which comprises the following steps of (1), (2) and (3).

In step (1), a slurry of starting materials as sources of elements used in the oxide catalyst of the present invention is prepared. Examples of sources of molybdenum, tungsten, bismuth, lanthanum, cerium, praseodymium, neodymium, samarium, europium, gadolinium, terbium, dysprosium, holmium, erbium, thulium, ytterbium, lutetium, yttrium, iron, cobalt, magnesium, nickel, potassium, rubidium and cesium include ammonium salts, nitrates, nitrites, chlorides, sulfates and organic acid salts of these elements, which are soluble in water or nitric acid. Especially, it is preferred that a molybdenum source and a tungsten source are ammonium salts. It is also preferred that sources of bismuth, lanthanum, cerium, praseodymium, neodymium, samarium, europium, gadolinium, terbium, dysprosium, holmium, erbium, thulium, ytterbium, lutetium, yttrium, iron, cobalt, magnesium, nickel, potassium, rubidium and cesium are nitrates or nitrites of these elements. As sources of antimony, there can be mentioned antimony pentaoxide, antimony trioxide and metallic antimony. From the viewpoint of availability, antimony trioxide is preferred as an antimony source.

With respect to the methods for preparing a slurry of starting materials as sources of elements, there is no particular limitation. For example, a slurry of starting materials can be prepared as follows. An aqueous suspension of ammonium molybdate, ammonium tungstate and antimony trioxide is prepared, and the prepared suspension is heated to 80° C. to 90° C. while stirring, followed by the addition of hydrogen peroxide, to thereby obtain solution 1 containing molybdenum, tungsten and antimony. On the other hand, nitrates or nitrites of other elements are dissolved in water or an aqueous solution of nitric acid to thereby obtain solution 2. The obtained solution 2 is mixed with the above-mentioned solution 1 containing molybdenum, tungsten and antimony, to thereby obtain a slurry of starting materials.

In step (2), the slurry obtained in the step (1) above is subjected to spray drying, to thereby obtain a spherical or quasispherical particulate catalyst precursor. The spray drying of the slurry can be conducted by a conventional method commercially employed, such as centrifugation, a two-phase flow nozzle method or a high pressure nozzle method, to obtain a dried particulate catalyst precursor. In this instance, it is preferred to use air which has been heated by an electric heater, steam or the like, as a heat source for drying. In this case, it is preferred that the entrance temperature of the dryer section of the spray dryer is from 150° C. to 400° C. By the use of the dried particulate catalyst precursor thus obtained, it becomes possible to obtain the oxide catalyst composition in the form of an extruded catalyst, or preferably in the form of a tableted catalyst which is preferred because of uniformity in shape and density thereof.

In step (3), the dried particulate catalyst precursor obtained in step (2) above is calcined and finally fired to thereby obtain a desired oxide catalyst composition. The dried particulate catalyst precursor is calcined at a temperature of from 180° C. to 400° C. for about 0.5 to 24 hours, and, if desired, the resultant calcined product is molded into an appropriate shape by extrusion molding or tableting, followed by final firing at a temperature of from 350° C. to 600° C. for 1 to 24 hours. For calcination and final firing, a kiln, such as a rotary kiln, a tunnel kiln or a muffle kiln, can be used.

From the viewpoint of improving the selectivity for the desired product, it is desired that no silica is used or, if used, the amount of silica in the oxide catalyst composition is as small as possible. However, when it is desired to increase the surface area of the oxide catalyst composition so as to improve the activity thereof, silica may be used in a limited amount. Examples of silica sources include silica sol, silica gel, and a silicate, such as potassium silicate or sodium silicate. In the oxide catalyst composition, it is preferred that the atomic ratio of silica, relative to twelve atoms of the total of molybdenum and tungsten, is 3 or less, more preferably 1 or less, still more preferably 0.1 or less, in terms of silicon (Si).

The oxide catalyst composition of the present invention is a catalyst for use in producing methacrolein or a mixture of methacrolein and methacrylic acid by reacting at least one member selected from the group consisting of isobutylene and t-butanol with a molecular oxygen-containing gas. With respect to the methods for producing methacrolein or a mixture of methacrolein and methacrylic acid by using the oxide catalyst composition of the present invention, there is no particular limitation. However, hereinbelow, an explanation is made with respect to a preferred method of using the oxide catalyst composition of the present invention.

The gaseous phase catalytic oxidation reaction of at least one member selected from the group consisting of isobutylene and t-butanol with a molecular oxygen-containing gas can be carried out by introducing a feedstock gas (comprising 1% to 10% by volume of isobutylene, t-butanol or a mixture thereof and 99% to 90% by volume of a gaseous mixture of a molecular oxygen-containing gas and a diluent gas) to a fixed bed reactor having a fixed catalyst bed of a (preferably tableted) catalyst comprised of the above-mentioned oxide catalyst composition, wherein the feedstock gas is introduced at a temperature of from 250° C. to 450° C. under a pressure of from atmospheric pressure to 5 atm and at a space velocity of from 400 to 4,000/hr (under normal temperature and pressure (NTP) conditions).

Examples of molecular oxygen-containing gases include pure oxygen gas, and an oxygen-containing gas, such as air. Examples of diluent gases include nitrogen, carbon dioxide, steam and a mixture thereof.

In the present invention, it is preferred that the volume ratio of the molecular oxygen-containing gas to the above-mentioned gaseous mixture of the molecular oxygen-containing gas and the diluent gas satisfy the requirements of the formula 0.04<molecular oxygen-containing gas/(molecular oxygen-containing gas+diluent gas)<0.3, and that the concentration of molecular oxygen in the feedstock gas is from 4% to 20% by volume.

For preventing the occurrence of coking on the catalyst composition, it is necessary that steam be contained in the feedstock gas. However, from the viewpoint of suppressing the by-production of carboxylic acids, such as methacrylic acid, acetic acid and acrylic acid, it is preferred that the concentration of steam in the diluent gas is reduced to a level as low as possible. It is preferred that the amount of steam in the feedstock gas is generally from more than 0% to 30% by volume.

The oxide catalyst composition of the present invention exhibits not only a prolonged catalyst life due to its excellent properties with respect to thermal stability and reduction resistance, but also excellent selectivity for the desired product. By the use of the oxide catalyst composition of the present invention for producing methacrolein or a mixture of methacrolein and methacrylic acid, it becomes possible to stably produce the desired product for a long time while holding down the amount of the by-produced impurities, e.g. diacetyl. Methacrolein produced using a conventional catalyst contains a large amount (several thousands ppm) of diacetyl. By contrast, it has been found that the diacetyl content of methacrolein produced by the use of the oxide catalyst composition of the present invention is as low as 900 ppm or less.

In addition, the present inventors have analyzed each of methacrolein and a mixture of methacrolein and methacrylic acid by gas chromatography. The results of the analysis are as follows. A peak ascribed to diacetyl is detected at a retention time of about 17.3 minutes, and also two unidentified peaks are, respectively, detected at retention times of about 22.0 minutes and about 39.2 minutes (these unidentified peaks are, respectively, designated "R1" and "R2"). The area of each of the peaks R1 and R2 has been compared to the peak area of diacetyl, and the percentages of the areas of R1 and R2, each based on the peak area of diacetyl, are, respectively, designated "S1" and "S2". From S1 and S2 values it has been found that both of R1 and R2 are ascribed to substances causative of discoloration. Specifically, it has been confirmed, by the studies of the present inventors, that, even in the case of methyl methacrylate containing by-produced diacetyl in an amount as low as 650 ppm, a discoloration tends to occur when S1 value is 50% or more and S2 value is 80% or more, each based on the peak area of diacetyl. The oxide catalyst composition of the present invention is capable of holding down not only the formation of diacetyl, but also the formation of the unidentified impurities to which R1 and R2 are ascribed.

The above-mentioned methacrolein or mixture of methacrolein and methacrylic acid, which has a very low content of impurities, is very useful as a raw material for producing methyl methacrylate having excellent transparency.

As the methods actually practiced for the commercial-scale production of methyl methacrylate, there can be mentioned a "via methacrylic acid process" comprising three reaction steps and a "direct ML-to-MMA process" comprising two reaction steps.

The via methacrylic acid process is described at pages 172 to 176 of "Sekiyu Kagaku Prosesu (Petrochemical Process)", published by Kodansha Scientific, Inc., Japan. The above-mentioned document states that the via methacrylic acid process comprises three reaction steps, that is, a first oxidation step, a second oxidation step and an esterification step. The first oxidation step is a step of subjecting at least one starting material selected from the group consisting of isobutylene and t-butanol to a gaseous phase catalytic oxidation reaction with molecular oxygen in the presence of a catalyst, to thereby obtain methacrolein. The second oxidation step is a step of subjecting the methacrolein obtained in the first oxidation step to a gaseous phase catalytic oxidation reaction with molecular oxygen in the presence of a catalyst, to thereby obtain methacrylic acid. The esterification step is a step of subjecting the methacrylic acid obtained in the second oxidation step to esterification, to thereby obtain methyl methacrylate.

The oxide catalyst composition of the present invention can be applied to the via methacrylic acid process in a manner in which the first oxidation step is performed using the oxide catalyst composition of the present invention to thereby produce methacrolein, and subsequently the second oxidation step and the esterification step are performed in a conventional manner, thereby obtaining methyl methacrylate. When the first oxidation step is performed using the oxide catalyst composition of the present invention, methacrolein having only low contents of impurities can be produced. Therefore, the adverse influences of such impurities on the methacrolein oxidation catalyst used in the second oxidation step (such as lowering of the catalytic activity and shortening of the catalyst life) can be decreased. In addition, the following should be noted. Since the reaction temperature used in the second oxidation step of the via methacrylic acid process is high, that is, 300° C. to 400° C., it is considered that most of the substances causative of discoloration which are contained in the methacrolein are decomposed during the second oxidation step of the via methacrylic acid process. However, since not all of the substances causative of discoloration are decomposed in the via methacrylic acid process, use of methacrolein containing no substances causative of discoloration is desired for producing excellent methyl methacrylate.

The direct ML-to-MMA process comprises two catalytic reaction steps, wherein the first reaction step comprises subjecting isobutylene and/or t-butanol as a starting material to a gaseous phase catalytic oxidation reaction with a molecular oxygen-containing gas in the presence of an oxide catalyst (hereinafter, this catalyst is frequently referred to as a "first stage catalyst") to thereby obtain methacrolein, and the second reaction step comprises subjecting the obtained methacrolein to a gaseous phase catalytic reaction with methanol and a molecular oxygen-containing gas in the presence of a carrier-supported catalyst containing palladium (hereinafter, this catalyst is frequently referred to as a "second stage catalyst"), to thereby produce methyl methacrylate (MMA) by one step directly from methacrolein (ML). The oxide catalyst composition of the present invention is useful as a first stage catalyst in the direct ML-to-MMA process. Specifically, production of methacrolein or a mixture of methacrolein and methacrylic acid, that is, the first reaction step, can be performed by the above-mentioned preferred method.

In the second reaction step of the direct ML-to-MMA process, the methacrolein obtained in the first reaction step is reacted with methanol, wherein the methacrolein used contains only small amounts of impurities, namely methacrolein produced using the oxide catalyst composition of the present invention, to thereby produce methyl methacrylate. As the second stage catalyst used in the second reaction step, there can be used palladium-containing catalysts disclosed in, for example, U.S. Pat. No. 4,249,019, Examined Japanese Patent Application Publication No. Sho 57-35859, U.S. Pat. No. 4,518,796 and International Publication No. WO 97/3751. In addition, the second reaction step can be conducted in accordance with the reaction modes disclosed in these patent documents. Specifically, methyl methacrylate can be produced by reacting molecular oxygen, methacrolein and methanol in the presence of a second stage catalyst under moderate reaction conditions wherein the reaction temperature is in the range of from room temperature to 100° C. Thus, the second reaction step of the direct ML-to-MMA process is conducted at a low temperature at which most of the impurities, e.g. diacetyl, do not undergo a reaction. As explained above in detail, when a conventional first stage catalyst is used in the first reaction step of the direct ML-to-MMA process, the impurities, e.g. diacetyl, are by-produced in a large amount. Production of methyl methacrylate containing only small amounts of the impurities causative of discoloration has for the first time become possible by using the oxide catalyst composition of the present invention as a first stage catalyst in the first reaction step. When the oxide catalyst composition of the present invention is used in the first reaction step, the methyl methacrylate obtained in the second reaction step has an extremely low impurity content and, thus, there is no need to repeatedly conduct the subsequent purification operation. As a result, the loss of methyl methacrylate becomes decreased, leading to a cost reduction. Accordingly, the oxide catalyst composition of the present invention is very advantageous for the commercial production of methyl methacrylate.

The first stage and second stage reactions of the direct ML-to-MMA process and the operation for purifying methyl methacrylate may be conducted in a continuous manner. As an example of a continuous reaction mode, there can be mentioned the reaction mode involved in the direct ML-to-MMA process conducted in the Examples of the present application for producing methyl methacrylate, that is, the process shown in the flow chart of the Figure.

Methyl methacrylate having excellent transparency can be produced by the direct ML-to-MMA process using the oxide catalyst composition of the present invention as a first stage catalyst. As apparent from the results of the Examples and Comparative Examples of the present application, methyl methacrylate monomer produced using the oxide catalyst composition of the present invention has an APHA value (determined in accordance with JIS-K6716) of not more than 5, and methyl methacrylate polymer obtained by polymerizing such methyl methacrylate monomer has a YI value (determined in accordance with JIS-K7103) of not more than 10.

Such methyl methacrylate polymer having excellent transparency can be used as a substitute for glass and quartz in application fields requiring high transparency, such as optical fibers, light guide plates and the like; thus, such highly transparent methyl methacrylate polymer has very high commercial value.

BEST MODE FOR CARRYING OUT THE INVENTION

Hereinbelow, the present invention will be described in more detail with reference to the following Examples and Comparative Examples, but they should not be construed as limiting the scope of the present invention.

The number of oxygen atoms in the oxide catalyst composition is determined depending on the valence requirements of the other elements present. Therefore, in Examples and Comparative Examples, the indication of oxygen atom in the oxide catalyst composition is omitted from the formula representing the oxide catalyst composition.

In the following Examples and Comparative Examples, various properties of the oxide catalyst composition were evaluated as follows.

<Conversion and Selectivity>

The conversion and selectivity used for evaluating the results of the reaction are defined as follows:

$$\text{Conversion } (\%) = \frac{\text{mole of isobutylene or t-butanol reacted}}{\text{mole of isobutylene or t-butanol charged}} \times 100$$

$$\text{Selectivity } (\%) = \frac{\text{mole of methacrolein or methacrylic acid formed}}{\text{mole of isobutylene or t-butanol reacted}} \times 100$$

Data used to calculate the conversion and selectivity were obtained by gas chromatography.

<Determination of the Impurities Causative of Discoloration>

The amounts of the impurities causative of discoloration, which are contained in methacrolein or a mixture of methacrolein and methacrylic acid, were determined by gas chromatography as follows. As an apparatus for gas chromatography, there was used gas chromatograph GC-17A (manufactured and sold by Shimadzu Corporation, Japan) which was equipped with a capillary column of 110 m in length. The capillary column was obtained by connecting in series the following three capillary columns each having an inner diameter of 0.25 mm: TC-1 (length: 60 m), DB-1 (length: 30 m) and TG-WAX (length: 20 m). The gas chromatography was conducted under conditions wherein the initial temperature of the column was 45° C., and, after maintaining the column at 45° C. for 30 minutes, the column temperature was elevated to 220° C. at a temperature elevation rate of 5° C./min, and maintained at 220° C. for 25 minutes. A sample for gas chromatography was prepared by condensing all of the gaseous product containing methacrolein or a mixture of methacrolein and methacrylic acid, to thereby obtain a condensate, and adding 1,2-dimethoxyethane as an internal standard to the obtained condensate.

When the gas chromatography was performed under the above-mentioned conditions, a peak ascribed to diacetyl was detected at a retention time of about 17.3 minutes. In addition, two unidentified peaks were, respectively, detected at retention times of about 22.0 minutes and about 39.2 minutes, and these unidentified peaks were, respectively, named "R1" and "R2". The area of each of the peaks R1 and R2 is compared to the peak area of diacetyl, and the percentages of the areas of R1 and R2, each based on the peak area of diacetyl, are, respectively, designated "S1" and "S2". The S1 and S2 values are, respectively, used as indices for the by-production of R1 and R2. (Hereinafter, for simplicity's sake, the unit "%" is omitted from the S1 and S2 values.)

For producing methyl methacrylate having excellent transparency by the direct ML-to-MMA process, it is preferred that the amount of diacetyl contained in methacrolein is not more than 900 ppm, more advantageously not more than 600 ppm.

<Evaluation of the Discoloration of a Methyl Methacrylate Monomer>

The level of discoloration of a methyl methacrylate monomer was evaluated in accordance with JIS-K6716. Several dilutions of a concentrated hydrochloric acid solution containing potassium hexachloroplatinate (IV) and cobalt chloride were prepared to obtain a set of standard solutions. The APHA value of a sample solution was determined by using the set of the standard solutions as a criterion, wherein the standard solutions had specific different APHA values respectively corresponding to the degrees of dilution of the hydrochloric acid solution. Specifically, distilled water was used as a standard solution for an APHA value of 0, and standard solutions for APHA values of 5, 10, 15 and 20 were prepared by using corresponding different dilutions of the hydrochloric acid solution, wherein the smaller the degree of dilution, the higher the APHA value. The APHA value of a methyl methacrylate monomer was evaluated by comparing the color of the methyl methacrylate monomer with those of the standard solutions, and the APHA value was used as an index for discoloration.

The degree of discoloration of a methyl methacrylate monomer is preferably 5 or less, in terms of the APHA value. A methyl methacrylate polymer having excellent transparency can be obtained by polymerizing such a methyl methacrylate monomer having an APHA value of 5 or less.

<Evaluation of the Discoloration of a Methyl Methacrylate Polymer>

The level of discoloration of a methyl methacrylate polymer, which is obtained by polymerizing a methyl methacrylate monomer, was evaluated in accordance with the tests described in JIS-K7103, namely the tests for determining the yellowness index and yellowing factor of plastics.

A test specimen which was a methyl methacrylate polymer plate having a length of 55 cm, a width of 10 cm, and a thickness of 5 mm was prepared as follows. A gasket was sandwiched between two glass plates, and the glass plates were clamped together with the gasket held therebetween, thereby forming a uniform thickness space between the two glass plates, wherein the space functions as a cavity. A methyl methacrylate monomer containing added thereto 0.05% by weight of 2,2'-azo-bisisobutyronitrile as a polymerization initiator was poured into the space between the two glass plates by using a funnel. The glass plates were clamped further so as to remove air remaining between the glass plates and, then, the methyl methacrylate sandwiched between the glass plates was hermetically sealed. The resultant structure (comprising a methyl methacrylate layer sandwiched between the glass plates) was placed in a warm water bath at 50±1° C. for 6 hours and, then, placed in a thermostat, constant temperature bath maintained at 115±1° C. for 2 hours, to effect a polymerization of the methyl methacrylate, thereby obtaining a methyl methacrylate polymer. The thus obtained methyl methacrylate polymer (polymer plate) was allowed to cool to room temperature, and the polymer plate (thickness: 5 mm) was released from the glass plates. The polymer plate was cut into a size of 55 cm in length and 10 cm in width. Then, the two opposite 10 cm-length edge surfaces of the polymer plate were polished using a file and a buff, to thereby obtain a test specimen.

The obtained test specimen was visually examined with respect to the 10 cm-length edge surfaces thereof. Further, the test specimen was analyzed by a long optical path type spectrotransmission colorimeter (ASA-2 Model, manufactured and sold by Nippon Denshoku Industries, Co., Ltd., Japan). From the data obtained using the long optical path type spectrotransmission colorimeter, the yellowness index (YI) was calculated in accordance with JIS-K7103 (describing the tests for determining the yellowness index and yellowing factor of plastics). The YI value was used as an index for the discoloration of a methyl methacrylate polymer.

A methyl methacrylate polymer having a yellowness index (YI) of not more than 10 is preferred because such a polymer has excellent transparency.

EXAMPLE 1

An oxide catalyst composition having a structure (in terms of atomic ratios of constituent metallic elements, relative to twelve atoms of the total of molybdenum and tungsten) represented by the formula:

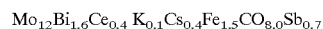

$$Mo_{12}Bi_{1.6}Ce_{0.4}K_{0.1}Cs_{0.4}Fe_{1.5}CO_{8.0}Sb_{0.7}$$

was prepared as follows.

Ammonium heptamolybdate in an amount of 350.0 g was dissolved in 1,700 g of water having a temperature of about 50° C., to thereby obtain an aqueous solution. To the obtained aqueous solution was added 16.8 g of antimony trioxide, thereby obtaining an aqueous suspension containing molybdenum and antimony. The obtained aqueous suspension was heated to 90° C. while stirring, and then 65.0 g of a 30% by weight aqueous hydrogen peroxide solution was slowly added thereto while stirring. The resultant mixture turned to assume bright yellow while foaming, and the state of the mixture became a solution. The stirring of the thus obtained aqueous solution was further continued for about 30 minutes at 90° C. Then, the solution was cooled to 50° C. and the solution was maintained at 50° C. (the thus obtained solution is referred to as "solution A"). On the other hand, 128.7 g of bismuth nitrate, 29.1 g of cerium nitrate, 1.66 g of potassium nitrate, 100.4 g of iron nitrate, 389.0 g of cobalt nitrate and 12.9 g of cesium nitrate were dissolved in 350 g of a 15% by weight aqueous nitric acid solution, to thereby obtain a solution (referred to as "solution B"). Solutions A and B were mixed together while stirring for about 2 hours, thereby obtaining a slurry of the starting materials. The obtained slurry was subjected to spray drying, to thereby obtain a dried, particulate catalyst composition precursor. The obtained dried, particulate catalyst composition precursor was calcined at 200° C. for 3 hours, to thereby obtain a calcined catalyst composition precursor in the form of a quasispherical particle. The obtained calcined catalyst composition precursor was molded into a columnar tablet having a diameter of 5.0 mm and a height of 4 mm, and the tablet was subjected to final firing at 520° C. for 3 hours, thereby obtaining a final tableted oxide catalyst composition.

Methacrolein was produced in order to evaluate the initial performances of the oxide catalyst composition. 4.0 g of the tableted oxide catalyst composition was charged into a stainless steel (SUS304) reaction tube which has a diameter of 10 mm and is provided with a jacket. A gaseous mixture of 6% by volume of isobutylene, 10.8% by volume of oxygen, 10.0% by volume of steam and 73.2% by volume of nitrogen was flowed to the reactor at a flow rate of 100 ml/min (NTP) while maintaining the internal temperature of the reactor at 350° C., thereby effecting a methacrolein synthesizing reaction and obtaining a gaseous product containing methacrolein. The results of the reaction were evaluated, and it was found that the conversion of isobutylene was 97.8%, the selectivity for methacrolein was 88.3% and the selectivity for methacrylic acid was 2.4%. The analysis of the condensed gaseous product showed that the production of diacetyl was 500 ppm, the S1 value was 10, and the S2 value was 52.

Subsequently, a test under stringent conditions was performed as follows. The reaction temperature was elevated to 480° C. and the flow rate of the above-mentioned gaseous mixture was changed to 220 ml/min (NTP), and a continuous operation for synthesizing methacrolein was conducted for 48 hours. Subsequently, the reaction conditions were changed back to the same conditions as in the reaction for the evaluation of the initial performances of the catalyst composition (reaction temperature: 350° C.; flow rate of gaseous mixture: 100 ml/min), and the results of the reaction are shown below. It was found that the performances of the catalyst composition under the stringent conditions were substantially the same as the initial performances. Specifically, the conversion of isobutylene was 97.8%, the selectivity for methacrolein was 88.3% and the selectivity for methacrylic acid was 2.4%. The analysis of the condensed gaseous product showed that the production of diacetyl was 490 ppm, the S1 value was 10, and the S2 value was 51.

In addition, using the above-mentioned oxide catalyst composition, methyl methacrylate was produced by the direct ML-to-MMA process in accordance with the steps as shown in the flow chart of Figure.

1. First Stage Reaction Step:

The first stage reaction was conducted in a manner as shown below, making reference to the reaction method of Example 1 of Unexamined Japanese Patent Application Laid-Open Specification No. Hei 9-323950.

The same tableted catalyst composition as prepared above was charged into a stainless steel (SUS304) reaction tube which has an outer diameter of 50.7 mm and an inner diameter of 46.7 mm and is provided with a jacket. Specifically, the reaction tube was packed with the tableted catalyst composition so as to form three catalyst layers therein, namely catalyst layers 1, 2 and 3 disposed in this order from the gas inlet to the gas outlet of the reaction tube, thereby providing reaction zones 1, 2 and 3 corresponding to catalyst layers 1, 2 and 3, respectively. The packing of the catalyst composition was performed so that the catalyst packing densities (C1, C2 and C3 respectively) of the catalyst layers 1, 2 and 3 became as follows: C1=800 kg/m$^3$, C2=400 kg/m$^3$ and C3=1,000 kg/m$^3$, and the heights (L1, L2 and L3 respectively) of the catalyst layers 1, 2 and 3 became as follows: L1=0.6 m, L2=1.5 m and L3=2.5 m. The adjustment of the catalyst packing densities of the catalyst layers 1, 2 and 3 was made by mixing a cylindrical porcelain Raschig ring (diameter: 5 mm, height: 4 mm, through-hole diameter: 3 mm) with the tableted catalyst.

The temperature of the heating medium of the jacket was set at 320° C., and a gaseous mixture of 5.75% by volume of t-butanol (TBA), 8.37% by volume of oxygen, 4.17% by volume of steam and 81.7% by volume of nitrogen (wherein the temperature of the gaseous mixture was 290° C.) was flowed to the reaction tube, and a methacrolein synthesizing reaction was conducted at a space velocity (SV) of 630 hr$^{-1}$, thereby preparing a gas containing methacrolein and steam. The maximum temperatures of the reaction zones 1, 2 and 3 were 383° C., 384° C. and 384° C., respectively. The conversion of t-butanol was 100%, the selectivity for methacrolein was 86.4% and the production of diacetyl was 500 ppm.

2. Methacrolein (MAL) Absorption Step:

Next, a methacrolein absorption step was conducted in a manner as shown below, wherein a quenching tower, a dehydration tower and an absorption tower were used, making reference to the disclosure of Unexamined Japanese Patent Application Laid-Open Specification No. Hei 11-80077 (corresponding to U.S. Pat. No. 5,969,178).

The methacrolein- and steam-containing gas prepared in step 1 above was introduced into a quenching tower. In the quenching tower, the gas was cooled to a temperature of 44° C. by means of water, so that a large portion of the steam and by-produced high boiling point substances and acids was removed from the gas, to thereby partially dehydrate the gas. The resultant partially dehydrated, methacrolein-containing gas had the following composition: 4.9 mol % of methacrolein, 2.7 mol % of water, 0.2 mol % of liquid by-products, such as acetone, and 92.2 mol % in total of nitrogen, oxygen, carbon dioxide and carbon monoxide gases and unreacted isobutylene.

The partially dehydrated, methacrolein-containing gas was fed into the bottom portion of a 30-stage plate dehydration tower (inner diameter: 10 cm, height: 5 m) provided with sieve trays at a flow rate of 3.6 Nm$^3$/hr, whereas a solution prepared by adding 100 ppm by weight of hydroquinone to liquid methanol was fed into the dehydration tower at the top plate thereof at a flow rate of 200 g/hr. The dehydration tower was operated under conditions wherein the temperature of the gas in the bottom portion of the dehydration tower was 44° C., the temperature of the gas in the uppermost portion of the dehydration tower was 18° C., the temperature of the liquid methanol solution was 18° C., and the pressure in the uppermost portion of the dehydration tower was 1.5 kg/cm$^2$. Thus, the partially dehydrated gas was dehydrated further under the above-mentioned conditions, and a dehydrated gaseous mixture containing methacrolein gas and methanol gas was obtained from the uppermost portion of the dehydration tower.

Subsequently, the dehydrated gaseous mixture obtained above was fed into the bottom gas phase portion of a 30-stage plate absorption tower (inner diameter: 10 cm, height: 5 m) provided with sieve trays, whereas a solution prepared by adding 100 ppm by weight of hydroquinone to liquid methanol was fed into the absorption tower at the top plate thereof at a flow rate of 900 g/hr. The absorption tower was operated under conditions wherein the temperature of the liquid in the bottom portion of the absorption tower was −6° C., the temperature of the liquid on the top plate was −3° C., the temperature of the liquid methanol solution was −3° C., and the pressure in the uppermost portion of the absorption tower was 1.4 kg/cm$^2$. Substantially all of the methacrolein gas and methanol gas which were contained in the dehydrated gaseous mixture was absorbed by liquid compounds under the above-mentioned conditions, thereby obtaining a liquid mixture (A) containing liquid methacrolein and liquid methanol from the bottom portion of the absorption tower. The obtained liquid mixture had the following composition: 31.7% by weight of methacrolein, 66.8% by weight of methanol, 0.7% by weight of water, and 0.8% by weight of by-products, such as acetone.

3. Second Stage Reaction Step:

The second stage catalyst was prepared in accordance with Reference Example 1 and Example 1 of International Patent Application Publication No. WO97/3751, as follows.

A catalyst intermediate was prepared in substantially the same manner as in Reference Example 1 of International Patent Application Publication No. WO97/3751. Aluminum nitrate and magnesium nitrate were dissolved in an aqueous silica sol (Snowtex N-30 (SiO$_2$ content: 30% by weight), manufactured and sold by Nissan Chemical Industries, Ltd., Japan) so that the Al/(Si+Al) proportion became 10 mol % and the Mg/(Si+Mg) proportion became 10 mol %. The resultant solution was subjected to spray drying at 130° C. using a spray dryer, thereby obtaining spherical particles having an average particle diameter of 60 μm. The obtained particles were calcined in air at 300° C. for 2 hours and subsequently at 600° C. for 3 hours, thereby obtaining a carrier for a catalyst. To the obtained carrier were added an aqueous solution of palladium chloride (15% by weight) and sodium chloride (10 t by weight) and an aqueous solution of lead nitrate (13% by weight) so that the amounts of the palladium chloride and lead nitrate contained in the resultant mixture became 5 parts by weight in terms of Pd atom and 6.5 parts by weight in terms of Pb atom, respectively. The resultant mixture was stirred at room temperature for 1 hour, thereby obtaining a carrier having adsorbed thereon almost all amounts of the palladium chloride and lead nitrate. Thereafter, to the obtained carrier having adsorbed thereon the palladium chloride and lead nitrate was dropwise added, while stirring, an aqueous solution containing hydrazine in a molar amount which is 3 times the total molar amount of the palladium chloride and lead nitrate adsorbed on the carrier, thereby reducing the palladium chloride and lead nitrate adsorbed on the carrier. Thus, a composition $Pd^{5.0}Pb^{6.5}/SiO_2$—$Al_2O_3$—$MgO$, wherein the superscript numerals at the right hand of Pd and Pb, respectively, represent parts by weight of Pd and Pb, relative to 100 parts by weight of the carrier, was obtained (hereinafter, the obtained composition is frequently referred to simply as "catalyst intermediate"). The analysis of the catalyst intermediate revealed that the atomic ratio of palladium to lead (Pd/Pb atomic ratio) was 3/1.95, and a maximum intensity peak at a diffraction angle (2θ) was 38.745° in the powder X-ray diffraction pattern thereof, and the ratio of the total intensity of two peaks ascribed to metallic palladium 3d electrons to the intensity of a peak ascribed to metallic lead 4f electrons in the X-ray photoelectron spectrum was 1/1.24.

Next, the catalyst intermediate was activated by the method as described in Example 1 of International Patent Application Publication No. WO97/3751, as follows. An external circulation type bubble column reactor (made of stainless steel) which was equipped with a separator for a catalyst and had a volume of 5.0 liters for a liquid phase, was charged with 1,200 g of the catalyst intermediate. A 36.7% by weight solution of methacrolein in methanol and a 2 to 4% by weight solution of NaOH in methanol were continuously fed to the reactor at flow rates of 2.16 liters/hr and 0.24 liter/hr, respectively (the methacrolein concentration of the reaction system comprised of the above-mentioned two different solutions was about 33% by weight), while introducing air into the reactor so that the oxygen concentration at the outlet of the reactor became 3.0% by volume (which is equivalent to the oxygen partial pressure of 0.15 kg/cm²), to effect an activation of the catalyst intermediate. The activation was conducted at a temperature of 80° C. under a pressure of 5 kg/cm². The concentration of NaOH in the above-mentioned methanol solution was controlled so that the reaction system had a pH of 7.1. The reaction mixture (activated catalyst) was continuously withdrawn from the outlet of the reactor at a rate of 2.4 liters/hr. The activation of the catalyst intermediate was completed after 50 hours from the start of the reaction. During the reaction, the reaction mixture fractions continuously withdrawn from the outlet of the reactor contained about 270 ppm of lead on the average. It is assumed that the reasons for this is that the lead contained in the catalyst is dissolved out in an ionized form thereof into the reaction system by the action of the meth- acrylic acid produced during the above reaction (the reaction mixture fractions continuously withdrawn from the outlet of the reactor contained 1.1% by weight of methacrylic acid on the average), and the formed lead ions are reduced with active hydrogen which is generated in the reaction between methacrolein and methanol. The analysis of the activated catalyst revealed that the Pd/Pb atomic ratio was 3/1.24, and a maximum intensity peak at a diffraction angle (2θ) was 38.652° in the powder X-ray diffraction pattern thereof.

The second stage reaction was conducted using the liquid mixture (A) obtained in step 2 above (methacrolein absorption step) and the above-prepared second stage catalyst, making reference to the Examples of Unexamined Japanese Patent Application Laid-Open Specification No. Hei 11-80077 (corresponding to U.S. Pat. No. 5,969,178).

Two external circulation type bubble column reactors (reactor I and reactor II which were made of stainless steel) each having a volume of 5.0 liters for a liquid phase were connected in series (i.e., reactor II was connected to reactor I). Each of reactors I and II was individually charged with 900 g of the activated second stage catalyst. The liquid mixture (A) obtained in step 2 above was fed into reactor I at a flow rate of 1,600 g/hr. In this instance, a solution of sodium hydroxide in methanol and a solution of lead acetate in methanol were also fed into each of reactors I and II so that the liquid in each reactor had a pH value of 6.1 and a lead concentration of 20% by weight. An oxidative esterification reaction of methacrolein was conducted at a temperature of 80° C. under a pressure of 3.0 kg/cm², wherein the oxygen partial pressures of the exhausted gases flowing out from the outlets of reactors I and II were 0.095 kg/cm² and 0.03 kg/cm², respectively. As a result, a reaction mixture (B) containing methyl methacrylate, water, methacrolein and methanol was obtained from the outlet of reactor II, and it was found that the conversion of methacrolein was 80.3% and the selectivity for methyl methacrylate was 90.7%.

4. Methacrolein (MAL) Recovery Step

Methacrolein recovery step was conducted as follows, making reference to Example 1 of Unexamined Japanese Patent Application Laid-Open Specification No. Hei 11-246453. The reaction mixture (B) containing methyl methacrylate, water, methacrolein and methanol, which was obtained in step 3 (second stage reaction step) above, was fed into a 45-stage plate distillation tower (inner diameter: 15 cm, height: 6 m) provided with sieve trays. The reaction mixture (B) was fed at the 30th plate as counted from the top of the distillation tower at a flow rate of 1,600 g/hr. Hydroquinone as a polymerization inhibitor was fed into the distillation tower at the top thereof at a rate such that the concentration of the polymerization inhibitor in the liquid falling inside the distillation tower became at least 100 ppm. The distillation tower was operated under conditions wherein the temperature at the uppermost portion of the distillation tower was 31° C., the temperature at the lowermost portion of the distillation tower was 84° C., the temperature at the 6th plate as counted from the bottom of the distillation tower was 81.4° C., and the pressure at the uppermost portion of the distillation tower was atmospheric pressure. As a result, a bottom liquid (C) containing methyl methacrylate was obtained from the bottom of the distillation tower.

5. Acid Treatment/Water-Oil Separation Step

The bottom liquid (C) obtained in step 4 above was fed into an oil-water phase separation vessel at a flow rate of 800 g/hr. Aqueous sulfuric acid was fed into the conduit for feeding bottom liquid (C) to the oil-water phase separation vessel so that the resultant aqueous phase in the oil-water phase separation vessel had a pH of 2.0. The mixture of bottom liquid (C) and sulfuric acid in the separation vessel was separated into an oil phase and an aqueous phase by centrifugation, and the oil phase was recovered and subjected to the subsequent high boiling point substance separation step. In this step 5, two separation vessels were used which were disposed so as to enable alternate use thereof for conducting the phase separation of the bottom liquid (C).

6. High Boiling Point Substance Separation Step

A high boiling point substance separation step was conducted as follows, making reference to Example 1 of Unexamined Japanese Patent Application Laid-Open Specification No. Hei 11-302224. The oil phase separated in step 5 above was fed into a 30-stage plate distillation tower (inner diameter: 10 cm, height: 5 m) provided with sieve trays at the 20th plate as counted from the top thereof at a flow rate of 600 g/hr. An apparatus comprising a brine refrigerator for removing a liquid under reduced pressure was provided at the top of the distillation tower, and an apparatus which was controlled by means of a level gauge and which comprised a refrigerator for withdrawing steam under reduced pressure and cooling the withdrawn steam to thereby obtain a condensate, was provided at the bottom of the distillation tower. The distillation tower was continuously operated under conditions wherein the reflux rate was 1,000 g/hr and the pressure at the uppermost portion of the distillation tower was 150 mmHg, while feeding a methyl methacrylate solution containing 5% by weight of hydroquinone from the top of the distillation tower at a flow rate of 40 g/hr. The temperatures at the uppermost portion and the lowermost portion of the distillation tower were 45° C. and 70° C., respectively. A steam containing methyl methacrylate was recovered from the top of the distillation tower and cooled by means of a refrigerator to thereby obtain a condensate. The condensate was withdrawn at a rate of 500 g/hr.

7. Low Boiling Point Substance Separation Step

A low boiling point substance separation step was conducted as follows, making reference to Example 1 of Unexamined Japanese Patent Application Laid-Open Specification No. Hei 11-35523. The condensate obtained in step 6 above was fed into a 30-stage plate distillation tower (inner diameter: 10 cm, height: 5 m) provided with sieve trays at the 10th plate as counted from the top thereof at a flow rate of 500 g/hr. An apparatus comprising a brine refrigerator for removing a liquid under reduced pressure was provided at the top of the distillation tower, and an apparatus which was controlled by means of a level gauge and which comprised a refrigerator for withdrawing steam under reduced pressure and cooling the withdrawn steam to thereby obtain a condensate, was provided at the bottom of the distillation tower. The distillation tower was continuously operated under conditions wherein the reflux rate was 400 g/hr and the pressure at the uppermost portion of the distillation tower was 250 mmHg, while feeding a methyl methacrylate solution containing 5% by weight of hydroquinone from the top of the distillation tower at a flow rate of 40 g/hr. The temperatures at the uppermost portion and the lowermost portion of the distillation tower were 50° C. and 80° C., respectively. A steam containing methyl methacrylate was recovered from the top of the distillation tower and cooled by means of a refrigerator to thereby obtain a condensate. The obtained condensate was withdrawn at a rate of 500 g/hr.

8. Methyl Methacrylate (MMA) Purification Step

The condensate obtained in step 7 above was fed into a 70-stage plate distillation tower (inner diameter: 10 cm, height: 5 m) provided with sieve trays at the 35th plate as counted from the top thereof at a flow rate of 500 g/hr. An apparatus comprising a brine refrigerator for removing a liquid under reduced pressure was provided at the top of the distillation tower, and an apparatus which was controlled by means of a level gauge and which comprised a refrigerator for withdrawing steam under reduced pressure and cooling the withdrawn steam to thereby obtain a condensate, was provided at the bottom of the distillation tower. The distillation tower was continuously operated under conditions wherein the reflux rate was 225 g/hr and the pressure at the uppermost portion of the distillation tower was 140 mmHg, while feeding a methyl methacrylate solution containing 5% by weight of hydroquinone from the top of the distillation tower at a flow rate of 40 g/hr. The temperatures at the uppermost portion and the lowermost portion of the distillation tower were 55° C. and 80° C., respectively. A steam containing methyl methacrylate was recovered from the top of the distillation tower and cooled by means of a refrigerator, thereby obtaining a purified methyl methacrylate at a flow rate of 450 g/hr.

The thus obtained purified methyl methacrylate had an APHA value of approximately 3, and a methyl methacrylate polymer produced using the methyl methacrylate monomer had a YI value of 3.5. Therefore, the methyl methacrylate monomer and methyl methacrylate polymer produced using the oxide catalyst composition of the present invention had excellent APHA value and excellent YI value, respectively.

COMPARATIVE EXAMPLE 1

An oxide catalyst composition having a structure (in terms of atomic ratios of constituent metallic elements, relative to twelve atoms of the total of molybdenum and tungsten) represented by the formula:

$Mo_{12}Bi_{1.6}Ce_{0.4}K_{0.1}Cs_{0.4}Fe_{1.5}CO_{8.0}$ was prepared as follows.

362 g of ammonium heptamolybdate was dissolved in 1,750 g of water having a temperature of about 50° C., to thereby obtain an aqueous solution (referred to as "solution A"). On the other hand, 133 g of bismuth nitrate, 30.1 g of cerium nitrate, 1.72 g of potassium nitrate, 103.9 g of iron nitrate, 402 g of cobalt nitrate and 13.4 g of cesium nitrate were dissolved in 355 g of a 15% by weight aqueous nitric acid solution, to thereby obtain a solution (referred to as "solution B"). Solutions A and B were mixed together while stirring for about 2 hours, thereby obtaining a slurry of the starting materials. The obtained slurry was subjected to spray drying, to thereby obtain a dried, particulate catalyst composition precursor. The obtained dried, particulate catalyst composition precursor was calcined at 200° C. for 3 hours, to thereby obtain a calcined catalyst composition precursor in the form of a quasispherical particle. The obtained calcined catalyst composition precursor was molded into a columnar tablet having a diameter of 5.0 mm and a height of 4 mm, and the tablet was subjected to final firing at 500° C. for 3 hours, thereby obtaining a final tableted oxide catalyst composition.

Methacrolein was produced in the same manner as in Example 1 in order to evaluate the initial performances of the oxide catalyst composition. The results of the reaction were evaluated, and it was found that the conversion of isobutylene was 97.4%, the selectivity for methacrolein was 86.5% and the selectivity for methacrylic acid was 2.4%. The analysis of the condensed gaseous product showed that the production of diacetyl was 3,500 ppm, the S1 value was 20, and the S2 value was 56.

Subsequently, a test under stringent conditions was performed in the same manner as in Example 1 to evaluate the performances of the catalyst composition under stringent conditions. It was found that the conversion of isobutylene was 97.4%, the selectivity for methacrolein was 86.3% and the selectivity for methacrylic acid was 2.4%. The analysis of the condensed gaseous product showed that the production of diacetyl was 3,600 ppm, the S1 value was 21, and the S2 value was 56.

In addition, a methyl methacrylate monomer was produced in the same manner as in Example 1 by the direct ML-to-MMA process by using the above-mentioned oxide catalyst composition. The thus obtained methyl methacrylate monomer had an APHA value of 8, and a methyl methacrylate polymer produced using the methyl methacrylate monomer had a YI value of 12.5. Therefore, the APHA value and YI value of the produced methyl methacrylate monomer and methyl methacrylate polymer were poor, as compared to those in the case of the use of the oxide catalyst composition of the present invention.

EXAMPLE 2

In Example 2, oxide catalyst composition having the formulations as shown in Table 1 was prepared in substantially the same manner as in Example 1, except that the amounts of metallic elements were adjusted so as to comply with the formulation indicated in Table 1. In addition, the final firing of the catalyst was conducted at the temperature indicated in Table 1.

The evaluation of the initial performances of the oxide catalyst composition and the stringent condition test were performed in the same manner as in Example 1. The initial performances of the catalyst composition are shown in Table 2 and the performances of the catalyst composition after the stringent condition test are shown in Table 3. In addition, a methyl methacrylate monomer was produced by the direct ML-to-MMA process in the same manner as in Example 1, and a methyl methacrylate polymer was produced using the thus produced methyl methacrylate monomer. The APHA value of the methyl methacrylate monomer and the YI value of the methyl methacrylate polymer are shown in Table 4.

EXAMPLE 3

An oxide catalyst composition having a structure (in terms of atomic ratios of constituent metallic elements, relative to twelve atoms of the total of molybdenum and tungsten) represented by the formula:

$$Mo_{9.5}W_{2.5}Bi_{1.7}Ce_{0.4}K_{0.2}Cs_{0.2}Fe_{1.0}Co_{6.5}Ni_{1.0}Sb_{0.5}$$

was prepared as follows.

103.6 g of ammonium paratungstate was dissolved in 1,900 g of water having a temperature of about 60° C., and 267.1 g of ammonium heptamolybdate was added thereto, thereby obtaining an aqueous solution. To the obtained aqueous solution was added 11.6 g of antimony trioxide, thereby obtaining an aqueous suspension containing molybdenum, tungsten and antimony. The obtained aqueous suspension was heated to 90° C. while stirring, and then 50.0 g of a 30% by weight aqueous hydrogen peroxide solution was slowly added thereto while stirring. The resultant mixture turned to assume bright yellow while foaming, and the state of the mixture became a solution. The stirring of the thus obtained aqueous solution was further continued for about 30 minutes at 90° C. Then, the solution was cooled to 50° C. and the solution was maintained at 50° C. (the thus obtained solution is referred to as "solution A"). On the other hand, 131.9 g of bismuth nitrate, 28.0 g of cerium nitrate, 3.21 g of potassium nitrate, 64.6 g of iron nitrate, 302.2 g of cobalt nitrate, 46.3 g of nickel nitrate and 6.23 g of cesium nitrate were dissolved in 280 g of a 15% by weight aqueous nitric acid solution, to thereby obtain a solution (referred to as "solution B"). Solutions A and B were mixed together while stirring for about 2 hours, thereby obtaining a slurry of the starting materials. The obtained slurry was subjected to spray drying, to thereby obtain a dried, particulate catalyst composition precursor. The obtained dried, particulate catalyst composition precursor was calcined at 200° C. for 3 hours, to thereby obtain a calcined catalyst composition precursor in the form of quasispherical particles. The obtained calcined catalyst composition precursor was molded into a columnar tablet having a diameter of 5.0 mm and a height of 4 mm, and the tablet was subjected to final firing at 520° C. for 3 hours, thereby obtaining a final tableted oxide catalyst composition.

The evaluation of the initial performances of the catalyst composition and the stringent condition test were performed in the same manner as in Example 1. The initial performances of the catalyst composition are shown in Table 2 and the performances of the catalyst composition after the stringent condition test are shown in Table 3. In addition, a methyl methacrylate monomer was produced by the direct ML-to-MMA process in the same manner as in Example 1, and a methyl methacrylate polymer was produced using the thus produced methyl methacrylate monomer. The APHA value of the methyl methacrylate monomer and the YI value of the methyl methacrylate polymer are shown in Table 4.

EXAMPLES 4 TO 20

In Examples 4 to 20, oxide catalyst compositions having respective formulations as shown in Table 1 were prepared in substantially the same manner as in Example 1 or Example 3, except that the sources of metallic elements and amounts thereof were selected so as to comply with the respective formulations indicated in Table 1. Specifically, the oxide catalyst compositions not containing tungsten were prepared in substantially the same manner as in Example 1, and the oxide catalyst compositions containing tungsten were prepared in substantially the same manner as in Example 3. In addition, the final firing of the catalysts was conducted at the respective temperatures indicated in Table 1.

The evaluation of the initial performances of the oxide catalyst compositions and the stringent condition tests were performed in the same manner as in Example 1. The initial performances of the catalyst compositions are shown in Table 2 and the performances of the catalyst compositions after the stringent condition test are shown in Table 3. In addition, methyl methacrylate monomers were produced by the direct ML-to-MMA process in the same manner as in Example 1, and methyl methacrylate polymers were produced using the respective methyl methacrylate monomers individually. The APHA values of the methyl methacrylate monomers and the YI values of the methyl methacrylate polymers are shown in Table 4.

COMPARATIVE EXAMPLES 2 TO 16

In Comparative Examples 2 to 16, oxide catalyst compositions having respective formulations as shown in Table 1 were prepared in substantially the same manner as in Comparative Example 1, Example 1 or Example 3, except that the sources of metallic elements and amounts thereof were selected so as to comply with the respective formulations indicated in Table 1. Specifically, the oxide catalyst compositions not containing antimony were prepared in substantially the same manner as in Comparative Example 1, the oxide catalyst compositions containing antimony, but not containing tungsten were prepared in substantially the same manner as in Example 1, and the oxide catalyst compositions containing antimony and tungsten were prepared in substantially the same manner as in Example 3. In addition, the final firing of the catalysts was conducted at the respective temperatures indicated in Table 1. The results of the evaluation of the initial performances of the oxide catalyst compositions are shown in Table 2.

Each of the oxide catalyst compositions of Comparative Examples 3, 6, 7 and 8, each of which exhibited a selectivity for methacrolein of 86.5% or more, was subjected to the stringent condition test in the same manner as in Example 1. The performances of the catalyst compositions after the stringent condition test are shown in Table 3. In addition, methyl methacrylate monomers were produced by the direct ML-to-MMA process in the same manner as in Example 1, and methyl methacrylate polymers were produced using the respective methyl methacrylate monomers. The APHA values of the methyl methacrylate monomers and the YI values of the methyl methacrylate polymers are shown in Table 4.

TABLE 1

Formulation of the catalyst compositions and the temperature used for final firing

| Formula (I) | $(Mo + W)_{12}$ | $Bi_a$ | $A_b$ | $B_c$ | $Fe_d$ | $X_e$ | $Sb_f$ | Temp. used for final firing (° C.) |
|---|---|---|---|---|---|---|---|---|
| Ex. 1 | $Mo_{12}$ | $Bi_{1.6}$ | $Ce_{0.4}$ | $K_{0.1} Cs_{0.4}$ | $Fe_{1.5}$ | $Co_{8.0}$ | $Sb_{0.7}$ | 520 |
| Ex. 2 | $Mo_{12}$ | $Bi_{1.2}$ | $Ce_{0.6}$ | $K_{0.2} Cs_{0.1} Rb_{0.3}$ | $Fe_{2.1}$ | $Co_{6.0} Mg_2$ | $Sb_{0.85}$ | 510 |
| Ex. 3 | $Mo_{9.5} W_{2.5}$ | $Bi_{1.7}$ | $Ce_{0.4}$ | $K_{0.2} Cs_{0.2}$ | $Fe_{1.0}$ | $Co_{6.5} Ni_1$ | $Sb_{0.5}$ | 520 |
| Ex. 4 | $Mo_{12}$ | $Bi_{0.24}$ | $Yb_{0.06}$ | $K_{0.1} Cs_{0.3}$ | $Fe_{2.4}$ | $Co_{8.0}$ | $Sb_{0.8}$ | 530 |
| Ex. 5 | $Mo_{11.6} W_{0.4}$ | $Bi_{0.3}$ | $Sm_{0.1}$ | $K_{1.0} Cs_{0.4}$ | $Fe_{2.1}$ | $Co_{7.0} Mg_2$ | $Sb_{0.5}$ | 510 |
| Ex. 6 | $Mo_{12}$ | $Bi_{0.4}$ | $Ce_{0.9}$ | $K_{0.4} Cs_{0.15}$ | $Fe_{1.9}$ | $Co_{8.0}$ | $Sb_{0.7}$ | 510 |
| Ex. 7 | $Mo_{11} W_1$ | $Bi_{0.55}$ | $La_{0.2}$ | $K_{0.2} Cs_{0.4}$ | $Fe_{2.6}$ | $Co_{8.0}$ | $Sb_{0.3}$ | 540 |
| Ex. 8 | $Mo_{11.7} W_{0.3}$ | $Bi_{0.55}$ | $Ce_{0.2}$ | $K_{0.1} Cs_{0.6}$ | $Fe_{2.2}$ | $Co_{5.6} Ni_{2.4}$ | $Sb_{1.9}$ | 510 |
| Ex. 9 | $Mo_{12}$ | $Bi_{2.0}$ | $Ce_{0.6}$ | $K_{0.5} Cs_{0.6}$ | $Fe_{4.0}$ | $Co_{6.0} Mg_{2.0} Ni_{1.0}$ | $Sb_{2.5}$ | 550 |
| Ex. 10 | $Mo_{12}$ | $Bi_{1.6}$ | $Y_{0.4}$ | $K_{0.1} Rb_{0.4}$ | $Fe_{1.5}$ | $Co_{8.0}$ | $Sb_{0.7}$ | 510 |
| Ex. 11 | $Mo_{10} W_2$ | $Bi_{1.6}$ | $Pr_{0.4}$ | $Cs_{0.4} Rb_{0.2}$ | $Fe_{1.5}$ | $Co_{8.0}$ | $Sb_{0.7}$ | 510 |
| Ex. 12 | $Mo_{12}$ | $Bi_{0.8}$ | $Sm_{0.9}$ | $K_{0.15} Cs_{0.35}$ | $Fe_{1.9}$ | $Co_{8.0}$ | $Sb_{1.4}$ | 520 |
| Ex. 13 | $Mo_{11.9} W_{0.1}$ | $Bi_{0.8}$ | $Nd_{0.5} Pr_{0.4}$ | $K_{0.15} Cs_{0.35}$ | $Fe_{1.9}$ | $Co_{8.0}$ | $Sb_{1.5}$ | 520 |
| Ex. 14 | $Mo_{12}$ | $Bi_{0.8}$ | $Ce_{0.9}$ | $K_{0.1} Cs_{0.1}$ | $Fe_{2.6}$ | $Co_{8.0}$ | $Sb_{0.8}$ | 520 |
| Ex. 15 | $Mo_{12}$ | $Bi_{0.6}$ | $Ce_{0.2}$ | $K_{0.1} Cs_{0.4}$ | $Fe_{1.9}$ | $Co_4 Mg_{4.0}$ | $Sb_{1.5}$ | 510 |
| Ex. 16 | $Mo_{12}$ | $Bi_{0.55}$ | $Ce_{0.15}$ | $K_{0.1} Cs_{0.4}$ | $Fe_{2.3}$ | $Co_{8.0}$ | $Sb_{0.85}$ | 530 |
| Ex. 17 | $Mo_{12}$ | $Bi_{0.55}$ | $Ce_{0.15}$ | $K_{0.1} Cs_{0.4}$ | $Fe_{1.3}$ | $Co_{5.0} Mg_{3.0}$ | $Sb_{0.85}$ | 510 |
| Ex. 18 | $Mo_{11} W_1$ | $Bi_{0.55}$ | $Ce_{0.15}$ | $K_{0.1} Cs_{0.4}$ | $Fe_{2.3}$ | $Co_{7.0}$ | $Sb_{1.5}$ | 530 |
| Ex. 19 | $Mo_{12}$ | $Bi_{0.9}$ | $Ce_{0.7}$ | $Rb_{0.5} Cs_{0.2}$ | $Fe_{3.1}$ | $Co_{7.0}$ | $Sb_{1.6}$ | 530 |
| Ex. 20 | $Mo_{12}$ | $Bi_1$ | $Ce_{0.9}$ | $Rb_{0.5}$ | $Fe_{3.5}$ | $Co_{11.0}$ | $Sb_{1.8}$ | 540 |
| Compara. Ex. 1 | $Mo_{12}$ | $Bi_{1.6}$ | $Ce_{0.4}$ | $K_{0.1} Cs_{0.4}$ | $Fe_{1.5}$ | $Co_{8.0}$ | | 500 |
| Compara. Ex. 2 | $Mo_8 W_4$ | $Bi_{1.6}$ | $Ce_{0.2}$ | $K_{0.1} Cs_{0.4}$ | $Fe_{1.5}$ | $Ni_{8.0}$ | | 510 |
| Compara. Ex. 3 | $Mo_{12}$ | $Bi_{0.16}$ | $Y_{0.04}$ | $K_{0.1} Cs_{0.3}$ | $Fe_{2.4}$ | $Co_{8.0}$ | $Sb_{0.8}$ | 510 |
| Compara. Ex. 4 | $Mo_{11} W_1$ | $Bi_{0.16}$ | $Sm_{0.04}$ | $K_{1.3} Cs_{0.2}$ | $Fe_{2.1}$ | $Co_{7.0} Mg_{2.0}$ | $Sb_{0.5}$ | 510 |
| Compara. Ex. 5 | $Mo_{11.5} W_{0.5}$ | $Bi_{0.3}$ | $Ce_{1.2}$ | $K_{0.15} Cs_{0.35}$ | $Fe_{1.9}$ | $Co_{8.0}$ | $Sb_{0.7}$ | 510 |
| Compara. Ex. 6 | $Mo_{12}$ | $Bi_{1.5}$ | $La_{0.03}$ | $K_{0.15} Cs_{0.35}$ | $Fe_{1.9}$ | $Co_{8.0}$ | $Sb_{0.7}$ | 510 |
| Compara. Ex. 7 | $Mo_{12}$ | $Bi_{0.55}$ | $Sm_{0.2}$ | $K_{0.2} Cs_{0.4}$ | $Fe_{2.6}$ | $Co_{8.0}$ | $Sb_{0.1}$ | 520 |
| Compara. Ex. 8 | $Mo_9 W_3$ | $Bi_{0.55}$ | $Nd_{0.2}$ | $K_{0.2} Cs_{0.4}$ | $Fe_{2.5}$ | $Co_{8.0}$ | $Sb_{2.4}$ | 520 |
| Compara. Ex. 9 | $Mo_{12}$ | $Bi_{2.0}$ | $Ce_{0.6}$ | $K_{0.5} Cs_{0.5}$ | $Fe_{5.0}$ | $Co_{10}$ | $Sb_{2.5}$ | 530 |
| Compara. Ex. 10 | $Mo_{11} W_1$ | $Bi_{1.6}$ | $Y_{0.4}$ | $K_{0.2} Cs_{0.5}$ | $Fe_{0.5}$ | $Co_{8.0} Mg_{2.0}$ | $Sb_{0.6}$ | 510 |
| Compara. Ex. 11 | $Mo_{12}$ | $Bi_{1.6}$ | $Pr_{0.4}$ | $K_{0.1} Cs_{0.4}$ | $Fe_{1.5}$ | $Co_{6.0} Ni_{3.0}$ | $Sb_{0.7}$ | 520 |
| Compara. Ex. 12 | $Mo_{12}$ | $Bi_{0.6}$ | $Ce_{0.2}$ | $K_{0.1} Cs_{0.1}$ | $Fe_{2.6}$ | $Co_2 Mg_{6.0}$ | $Sb_{0.8}$ | 510 |
| Compara. Ex. 13 | $Mo_{12}$ | $Bi_{2.0}$ | $Ce_{0.6}$ | $K_{0.5} Cs_{0.6}$ | $Fe_{4.0}$ | $Co_{6.0} Mg_{2.0} Ni_{1.0}$ | $Sb_{3.0}$ | 550 |
| Compara. Ex. 14 | $Mo_{12}$ | $Bi_{1.6}$ | $Ce_{0.4}$ | $K_{0.1} Rb_{0.4}$ | $Fe_{1.5}$ | $Ni_{8.0}$ | $Sb_{0.7}$ | 520 |
| Compara. Ex. 15 | $Mo_{12}$ | $Bi_{1.6}$ | $Ce_{0.4}$ | $K_{0.1} Rb_{0.4}$ | $Fe_{1.5}$ | $Co_{2.0} Mg_{2.0} Ni_{6.0}$ | $Sb_{0.7}$ | 520 |
| Compara. Ex. 16 | $Mo_{12}$ | $Bi_{1.6}$ | $Ce_{0.4}$ | $K_{0.1} Ce_{0.4}$ | $Fe_{1.5}$ | $Co_{10.0} Mg_{3.0}$ | $Sb_{0.7}$ | 540 |

TABLE 2

Evaluation of the initial performances of the oxide catalyst composition

| | Conversion of isobutylene (%) | Selectivity for methacrolein (%) | Selectivity for methacrylic acid (%) | Production of diacetyl (ppm) | Intensity of R1* (S1) | Intensity of R2* (S2) |
|---|---|---|---|---|---|---|
| Ex. 1 | 97.8 | 88.3 | 2.4 | 500 | 10 | 52 |
| Ex. 2 | 97.5 | 88.5 | 2.3 | 460 | 8 | 53 |
| Ex. 3 | 98.0 | 88.1 | 2.6 | 510 | 12 | 49 |
| Ex. 4 | 97.0 | 87.9 | 2.1 | 720 | 6 | 41 |

TABLE 2-continued

Evaluation of the initial performances of the oxide catalyst composition

|  | Conversion of isobutylene (%) | Selectivity for methacrolein (%) | Selectivity for methacrylic acid (%) | Production of diacetyl (ppm) | Intensity of R1* (S1) | Intensity of R2* (S2) |
|---|---|---|---|---|---|---|
| Ex. 5 | 97.2 | 88.0 | 2.2 | 640 | 7 | 45 |
| Ex. 6 | 97.4 | 88.1 | 2.2 | 610 | 9 | 49 |
| Ex. 7 | 97.7 | 88.6 | 2.4 | 400 | 10 | 50 |
| Ex. 8 | 97.9 | 88.5 | 2.4 | 350 | 12 | 48 |
| Ex. 9 | 96.9 | 88.2 | 2.1 | 620 | 8 | 42 |
| Ex. 10 | 97.9 | 87.9 | 2.0 | 560 | 11 | 41 |
| Ex. 11 | 97.8 | 88.1 | 2.2 | 540 | 13 | 48 |
| Ex. 12 | 97.6 | 88.4 | 2.5 | 490 | 7 | 39 |
| Ex. 13 | 97.5 | 88.3 | 2.4 | 550 | 9 | 37 |
| Ex. 14 | 97.6 | 88.0 | 2.6 | 400 | 11 | 44 |
| Ex. 15 | 97.7 | 88.2 | 2.3 | 450 | 10 | 41 |
| Ex. 16 | 97.6 | 88.3 | 2.3 | 380 | 8 | 43 |
| Ex. 17 | 97.0 | 88.0 | 2.2 | 430 | 11 | 46 |
| Ex. 18 | 97.3 | 87.9 | 2.4 | 420 | 10 | 48 |
| Ex. 19 | 97.4 | 88.1 | 2.3 | 470 | 9 | 39 |
| Ex. 20 | 97.1 | 87.9 | 2.3 | 490 | 12 | 46 |
| Compara. Ex. 1 | 97.4 | 86.5 | 2.4 | 3500 | 20 | 56 |
| Compara. Ex. 2 | 97.1 | 84.4 | 2.5 | 2460 | 18 | 55 |
| Compara. Ex. 3 | 97.2 | 86.6 | 2.3 | 1810 | 22 | 53 |
| Compara. Ex. 4 | 96.8 | 86.1 | 2.1 | 1560 | 27 | 59 |
| Compara. Ex. 5 | 97.1 | 85.8 | 2.3 | 1710 | 26 | 56 |
| Compara. Ex. 6 | 97.2 | 86.5 | 2.1 | 1660 | 25 | 55 |
| Compara. Ex. 7 | 97.3 | 86.6 | 2.2 | 2440 | 28 | 54 |
| Compara. Ex. 8 | 97.5 | 86.6 | 2.3 | 2830 | 21 | 53 |
| Compara. Ex. 9 | 98.2 | 84.0 | 2.5 | 3130 | 19 | 51 |
| Compara. Ex. 10 | 95.4 | 86.0 | 2.1 | 4640 | 32 | 60 |
| Compara. Ex. 11 | 97.2 | 85.5 | 2.2 | 1350 | 18 | 51 |
| Compara. Ex. 12 | 95.2 | 86.0 | 2.1 | 950 | 19 | 51 |
| Compara. Ex. 13 | 97.1 | 84.5 | 2.6 | 1030 | 17 | 49 |
| Compara. Ex. 14 | 97.2 | 84.7 | 2.5 | 2390 | 17 | 53 |
| Compara. Ex. 15 | 96.9 | 85.1 | 2.4 | 2160 | 20 | 51 |
| Compara. Ex. 16 | 97.5 | 84.9 | 2.3 | 2740 | 19 | 48 |

*S1 and S2 (which are, respectively, the percentages of the areas of R1 and R2, each based on the peak area of diacetyl) were used as indices for the intensities of R1 and R2.

TABLE 3

Evaluation of the oxide catalyst composition after the stringent condition test

|  | Conversion of isobutylene (%) | Selectivity for methacrolein (%) | Selectivity for methacrylic acid (%) | Production of diacetyl (ppm) | Intensity of R1* (S1) | Intensity of R2* (S2) |
|---|---|---|---|---|---|---|
| Ex. 1 | 97.8 | 88.3 | 2.4 | 490 | 10 | 51 |
| Ex. 2 | 97.5 | 88.5 | 2.3 | 400 | 7 | 50 |
| Ex. 3 | 98.0 | 88.1 | 2.6 | 440 | 11 | 48 |
| Ex. 4 | 97.0 | 88.0 | 2.1 | 630 | 6 | 39 |
| Ex. 5 | 97.2 | 88.1 | 2.2 | 640 | 7 | 42 |
| Ex. 6 | 97.4 | 88.1 | 2.2 | 510 | 8 | 47 |
| Ex. 7 | 97.7 | 88.6 | 2.4 | 350 | 9 | 49 |
| Ex. 8 | 97.9 | 88.6 | 2.4 | 310 | 12 | 46 |
| Ex. 9 | 96.9 | 88.2 | 2.1 | 540 | 7 | 37 |
| Ex. 10 | 97.9 | 88.0 | 2.0 | 480 | 9 | 37 |
| Ex. 11 | 97.8 | 87.9 | 2.2 | 490 | 12 | 46 |
| Ex. 12 | 97.6 | 88.4 | 2.5 | 440 | 6 | 37 |
| Ex. 13 | 97.5 | 88.3 | 2.4 | 500 | 8 | 35 |
| Ex. 14 | 97.6 | 88.0 | 2.6 | 390 | 11 | 42 |
| Ex. 15 | 97.7 | 88.3 | 2.3 | 440 | 9 | 41 |
| Ex. 16 | 97.6 | 88.3 | 2.3 | 370 | 9 | 44 |
| Ex. 17 | 97.0 | 88.0 | 2.2 | 430 | 11 | 46 |
| Ex. 18 | 97.3 | 87.9 | 2.4 | 410 | 10 | 49 |
| Ex. 19 | 97.4 | 88.1 | 2.3 | 470 | 9 | 39 |
| Ex. 20 | 97.1 | 87.9 | 2.3 | 490 | 12 | 45 |
| Compara. Ex. 1 | 97.4 | 86.3 | 2.4 | 3600 | 21 | 56 |
| Compara. Ex. 3 | 97.2 | 86.6 | 2.2 | 1830 | 24 | 54 |
| Compara. Ex. 6 | 96.3 | 86.4 | 2.1 | 1680 | 27 | 56 |
| Compara. Ex. 7 | 97.3 | 86.5 | 2.2 | 2480 | 28 | 55 |
| Compara. Ex. 8 | 97.4 | 86.6 | 2.2 | 2850 | 22 | 53 |

*S1 and S2 (which are, respectively, the percentages of the areas of R1 and R2, each based on the peak area of diacetyl) were used as indices for the intensities of R1 and R2.

TABLE 4

APHA values of methyl methacrylate monomers and
YI values of methyl methacrylate polymers

| | APHA of methyl methacrylate monomer | YI of methyl methacrylate polymer |
|---|---|---|
| Ex. 1 | 3 | 3.5 |
| Ex. 2 | 3 | 3.2 |
| Ex. 3 | 3 | 3.5 |
| Ex. 4 | 5 | 5.0 |
| Ex. 5 | 4 | 4.5 |
| Ex. 6 | 4 | 4.4 |
| Ex. 7 | 3 | 3.1 |
| Ex. 8 | 2 | 2.7 |
| Ex. 9 | 4 | 4.4 |
| Ex. 10 | 3 | 3.9 |
| Ex. 11 | 3 | 3.7 |
| Ex. 12 | 3 | 3.5 |
| Ex. 13 | 3 | 3.7 |
| Ex. 14 | 3 | 3.0 |
| Ex. 15 | 3 | 3.2 |
| Ex. 16 | 2 | 2.9 |
| Ex. 17 | 3 | 3.2 |
| Ex. 18 | 3 | 3.2 |
| Ex. 19 | 3 | 3.3 |
| Ex. 20 | 3 | 3.3 |
| Compara. Ex. 1 | 8 | 12.5 |
| Compara. Ex. 2 | 8 | 12.0 |
| Compara. Ex. 3 | 7 | 11.8 |
| Compara. Ex. 4 | 7 | 11.5 |
| Compara. Ex. 5 | 7 | 11.7 |
| Compara. Ex. 6 | 7 | 11.7 |
| Compara. Ex. 7 | 8 | 12.0 |
| Compara. Ex. 8 | 8 | 12.2 |
| Compara. Ex. 9 | 8 | 12.3 |
| Compara. Ex. 10 | 9 | 13.4 |
| Compara. Ex. 11 | 7 | 11.3 |
| Compara. Ex. 12 | 6 | 10.5 |
| Compara. Ex. 13 | 7 | 11.0 |
| Compara. Ex. 14 | 8 | 12.0 |
| Compara. Ex. 15 | 8 | 12.0 |
| Compara. Ex. 16 | 8 | 12.2 |

As apparent from the results shown in Tables 2 to 4 above, in the case of the production of methacrolein in the Examples, not only the amount of by-produced diacetyl, but also the amounts of the impurities to which R1 and R2 are ascribed were low. Further, when methyl methacrylate was produced by the direct ML-to-MMA process performed using the oxide catalyst composition of the present invention as a first stage catalyst, the produced methyl methacrylate monomer suffered substantially no discoloration. In addition, the polymer obtained by polymerizing the methyl methacrylate monomer also suffered substantially no discoloration. As apparent from Table 3 above, even in the stringent condition test in which methacrolein was produced at a high temperature, each of the oxide catalyst compositions produced in the Examples exhibited a high selectivity for methacrolein, which was substantially the same as the initial performances, and also the by-production of diacetyl and the impurities to which R1 and R2 are ascribed was low. Therefore, as compared to the conventional oxide catalyst compositions, the oxide catalyst composition of the present invention by-produces only small amounts of impurities and exhibits excellent properties with respect to thermal stability and reduction resistance.

INDUSTRIAL APPLICABILITY

The oxide catalyst composition of the present invention exhibits not only a prolonged catalyst life due to its excellent properties with respect to thermal stability and reduction resistance, but also excellent selectivity for the desired product. By the use of the oxide catalyst composition of the present invention for producing methacrolein or a mixture of methacrolein and methacrylic acid, it becomes possible to stably produce the desired product for a long time while holding down the amount of by-produced impurities, e.g. diacetyl. The produced methacrolein or mixture of methacrolein and methacrylic acid has low contents of the by-produced impurities, e.g. diacetyl, and such methacrolein or mixture of methacrolein and methacrylic acid is very advantageous as a raw material for producing methyl methacrylate having excellent transparency. A methyl methacrylate polymer having excellent transparency, which can be obtained by polymerizing such highly transparent methyl methacrylate monomer, can be advantageously used as a substitute for glass and quartz in application fields requiring high transparency, such as optical fibers, light guide plates and the like; thus, such highly transparent methyl methacrylate polymer has very high commercial value.

The invention claimed is:

1. An oxide catalyst composition for use in producing methacrolein or a mixture of methacrolein and methacrylic acid by reacting at least one member selected from the group consisting of isobutylene and t-butanol with a molecular oxygen-containing gas, said oxide catalyst composition being represented by the following formula (I):

$$(Mo+W)_{12}Bi_aA_bB_cFe_dX_eSb_fO_g \qquad (I)$$

wherein:
   A is at least one member selected from the group consisting of lanthanum, cerium, praseodymium, neodymium, samarium, europium, gadolinium, terbium, dysprosium, holmium, erbium, thulium, ytterbium, lutetium and lyttrium;
   B is at least one member selected from the group consisting of potassium, rubidium and cesium;
   X is cobalt solely, or a mixture of cobalt and at least one member selected from the group consisting of magnesium and nickel;
   wherein the number of molybdenum (Mo) atoms is in the range of from more than 9 to 12, and the number of tungsten (W) atoms is in the range of from 0 to less than 3, each relative to twelve atoms of the total of molybdenum (Mo) and tungsten (W); and
   a, b, c, d, e, f and g are, respectively, the atomic ratios of bismuth (Bi), A, B, iron (Fe), X, antimony (Sb) and oxygen (O), relative to twelve atoms of the total of molybdenum (Mo) and tungsten (W),
   wherein
   $0 < a \leq 8$,
   $0 < b \leq 8$,
   $0 < c \leq 3$,
   $0.2 < d < 5$,
   $1 \leq e \leq 12$,
   $0.1 < f < 3$, and
   g is the number of oxygen atoms required to satisfy the valence requirements of the other elements present; and
   wherein a, b, c, d and f satisfy the requirements of the following formulae:

$0.02 < b/(a+b+c) < 0.6$, $0 < c/(a+b+c) \leq 0.9$, $0.01 < d/(a+b+d) \leq 0.9$, and $0.1 < d-f < 2.5$.

2. The oxide catalyst composition according to claim 1, wherein, in said mixture X in formula (I), the atomic ratio of cobalt to the total of cobalt, magnesium and nickel is 0.5 or more, wherein, when said mixture X in formula (I) contains magnesium, the atomic ratio of magnesium to the total of cobalt, magnesium and nickel in said mixture X is 0.5 or less, and wherein, when said mixture X in formula (I) contains nickel, the atomic ratio of nickel to the total of cobalt, magnesium and nickel in said mixture X is less than 0.33.

3. The oxide catalyst composition according to claim 1 or 2, wherein a, b and c in formula (I) satisfy the requirements of the formula: $0.05 < b/(a+b+c) < 0.5$.

4. The oxide catalyst composition according to claim 1 or 2, wherein a, b and c in formula (I) satisfy the requirements of the formula: $0.1 < c/(a+b+c) < 0.8$.

5. The oxide catalyst composition according to claim 1 or 2, wherein a, b, d and f in formula (I) satisfy the requirements of the formulae:

$$0.2 < d/(a+b+d) < 0.9 \text{ and } 0.3 \leq d-f \leq 2.3.$$

6. A method for producing methacrolein or a mixture of methacrolein and methacrylic acid, which comprises reacting at least one member selected from the group consisting of isobutylene and t-butanol with a molecular oxygen-containing gas in the presence of the oxide catalyst composition of claim 1 or 2, thereby obtaining methacrolein or a mixture of methacrolein and methacrylic acid.

7. A method for producing methyl methacrylate, which comprises:

(i) reacting at least one member selected from the group consisting of isobutylene and t-butanol with a molecular oxygen-containing gas in the presence of the oxide catalyst composition of claim 1 or 2, to thereby obtain methacrolein;

(ii) subjecting the obtained methacrolein to a gaseous phase catalytic oxidation reaction with molecular oxygen, to thereby obtain methacrylic acid; and (iii) subjecting the obtained methacrylic acid to an esterification with methanol, thereby obtaining methyl methacrylate.

8. A method for producing methyl methacrylate, which comprises:

(i) reacting at least one member selected from the group consisting of isobutylene and t-butanol with a molecular oxygen-containing gas in the presence of the oxide catalyst composition of claim 1 or 2, to thereby obtain methacrolein; and (ii) reacting the obtained methacrolein with methanol, thereby obtaining methyl methacrylate.

* * * * *